US008436161B2

(12) United States Patent
Conner et al.

(10) Patent No.: US 8,436,161 B2
(45) Date of Patent: May 7, 2013

(54) CHIMERIC PROMOTERS COMPRISING A RICE ACTIN 1 PROMOTER AND 35S ENHANCER FOR USE IN PLANTS

(75) Inventors: Timothy W. Conner, Chesterfield, MO (US); Stanislaw Flasinski, Chesterfield, MO (US); Sheng Z. Pang, Chesterfield, MO (US); Jinsong You, Manchester, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 12/876,071

(22) Filed: Sep. 3, 2010

(65) Prior Publication Data

US 2011/0077223 A1 Mar. 31, 2011

Related U.S. Application Data

(60) Division of application No. 12/023,350, filed on Jan. 31, 2008, now Pat. No. 7,838,652, which is a continuation of application No. 11/038,981, filed on Jan. 20, 2005, now Pat. No. 7,371,848.

(60) Provisional application No. 60/537,793, filed on Jan. 20, 2004.

(51) Int. Cl.
*C12N 15/82* (2006.01)
*C07H 21/04* (2006.01)
*A01H 5/00* (2006.01)

(52) U.S. Cl.
USPC ......... 536/24.1; 536/23.1; 800/298; 800/295; 800/288; 800/300; 435/320.1; 435/419; 435/468

(58) Field of Classification Search ........................ None
See application file for complete search history.

(56) References Cited

U.S. PATENT DOCUMENTS 3,853,530 A 12/1974 Franz
5,097,025 A * 3/1992 Benfey et al. ................ 536/23.6
5,362,865 A 11/1994 Austin
5,530,196 A 6/1996 Fraley et al.
5,641,876 A 6/1997 McElroy et al.
6,051,753 A 4/2000 Comai et al.
6,429,357 B1 8/2002 McElroy et al.
6,448,476 B1 9/2002 Barry
6,462,258 B1 10/2002 Fincher et al.
6,489,542 B1 12/2002 Corbin et al.
6,569,122 B2 5/2003 Fischer et al.
6,660,911 B2 12/2003 Fincher et al.
6,670,467 B2 12/2003 Barbour et al.
6,689,880 B2 2/2004 Chen et al.
6,759,575 B2 7/2004 Michiels et al.
6,919,495 B2 7/2005 Fincher et al.
7,371,848 B2 * 5/2008 Conner et al. ............... 536/24.1
7,622,632 B2 11/2009 Ursin et al.
7,838,652 B2 * 11/2010 Conner et al. .............. 536/24.1
2002/0062503 A1 5/2002 Chen et al.
2002/0144304 A1 10/2002 Fincher et al.
2003/0199681 A1 10/2003 Fincher et al.
2006/0156435 A1 7/2006 Ursin et al.

FOREIGN PATENT DOCUMENTS

WO WO 00/11185 * 3/2000
WO WO 00/11185 A2 3/2000
WO WO 00/29596 * 5/2000
WO WO 00/29596 A1 5/2000
WO WO 01/44457 A2 6/2001

OTHER PUBLICATIONS

Benfey et al., "Tissue-specific expression from CaMV 35S enhancer subdomains in early stages of plant development," *EMBO J.*, 9(6):1677-1684, 1990.

Kay et al., "Duplication of CaMV 35S promoter sequences created a strong enhancer for plant genes," *Science*, 236:1299-1302, 1987.

Lam et al., "Site-specific mutations alter in vitro factor binding and change promoter expression pattern in transgenic plants," *Proc. Natl. Acad. Sci. USA*, 86:7890-7894, 1989.

Omirulleh et al., "Activity of a chimeric promoter with the double CaMV 35S enhancer element in protoplast-derived cells and transgenic plants in maize," *Plant Mol. Biol.*, 21:415-428, 1993.

* cited by examiner

*Primary Examiner* — Cathy Kingdon Worley
(74) *Attorney, Agent, or Firm* — Dentons US LLP; Erin Robert

(57) ABSTRACT

The present invention provides polynucleotide molecules useful for expressing transgenes in plants. More particularly, the present invention provides chimeric promoters comprising rice actin 1 promoters fused with Cauliflower mosaic virus 35S enhancers. The present invention also provides expression constructs containing the chimeric promoter. The present invention also provides transgenic plants and seeds containing the chimeric promoter.

15 Claims, 3 Drawing Sheets

CaMV 35S promoter enhancer domains

4xB3 four tandem copies of B3 domain (-208 to -155)

4xAS-1 four tandem copies of the activation sequence (-83 to -62)

2xB1-B2 two tandem copies of B1-B2 domain (-148 to -90)

2xA1-B3 two tandem copies of A1-B3 domain (-208 to -46)

2xB1-B5 two tandem copies of B1-B5 domain (-343 to -90)

SEQUENCE LISTING

<160> NUMBER OF SEQ ID NOS: 35

<210> SEQ ID NO 1
<211> LENGTH: 612
<212> TYPE: DNA
<213> ORGANISM: Cauliflower mosaic virus

<400> SEQUENCE: 1

```
ggtccgattg agacttttca acaaagggta atatccggaa acctcctcgg attccattgc     60

ccagctatct gtcactttat tgtgaagata gtggaaaagg aaggtggctc ctacaaatgc    120

catcattgcg ataaaggaaa ggccatcgtt gaagatgcct ctgccgacag tggtcccaaa    180

gatggacccc cacccacgag gagcatcgtg gaaaaagaag acgttccaac cacgtcttca    240

aagcaagtgg attgatgtga tggtccgatt gagacttttc aacaaagggt aatatccgga    300

aacctcctcg gattccattg cccagctatc tgtcacttta ttgtgaagat agtggaaaag    360

gaaggtggct cctacaaatg ccatcattgc gataaaggaa aggccatcgt tgaagatgcc    420

tctgccgaca gtggtcccaa agatggaccc ccacccacga ggagcatcgt ggaaaaagaa    480

gacgttccaa ccacgtcttc aaagcaagtg gattgatgtg atatctccac tgacgtaagg    540

gatgacgcac aatcccacta tccttcgcaa gacccttcct ctatataagg aagttcattt    600

catttggaga gg                                                         612
```

<210> SEQ ID NO 2
<211> LENGTH: 240
<212> TYPE: DNA
<213> ORGANISM: Cauliflower mosaic virus

<400> SEQUENCE: 2

```
catcgttgaa gatgcctctg ccgacagtgg tcccaaagat ggacccccac ccacctcgac     60

catcgttgaa gatgcctctg ccgacagtgg tcccaaagat ggacccccac ccacctcgac    120

catcgttgaa gatgcctctg ccgacagtgg tcccaaagat ggacccccac ccacctcgac    180

catcgttgaa gatgcctctg ccgacagtgg tcccaaagat ggacccccac ccacctcgac    240
```

<210> SEQ ID NO 3
<211> LENGTH: 221
<212> TYPE: DNA
<213> ORGANISM: Cauliflower mosaic virus

<400> SEQUENCE: 3

```
agcttctgac gtaagggatg acgcacctga cgtaagggat gacgcacctg acgtaaggga     60

tgacgcacct gacgtaaggg atgacgcact cgagatcccc atctccactg acgtaaggga    120

tgacgcacaa tcccactatc cttcgcaaga cccttcctct atataaggaa gttcatttca    180

tttggagagg acacgctgac aagctagctt ggctgcaggt a                        221
```

<210> SEQ ID NO 4
<211> LENGTH: 125
<212> TYPE: DNA
<213> ORGANISM: Cauliflower mosaic virus

<400> SEQUENCE: 4

```
catcgtggaa aaagaagacg ttccaaccac gtcttcaaag caagtggatt gatgtgataa     60

gctcctcatc gtggaaaaag aagacgttcc aaccacgtct tcaaagcaag tggattgatg    120

tgata                                                                125
```

<210> SEQ ID NO 5
<211> LENGTH: 332
<212> TYPE: DNA
<213> ORGANISM: Cauliflower mosaic virus

<400> SEQUENCE: 5
catcgttgaa gatgcctctg ccgacagtgg tcccaaagat ggacccccac ccacgaggag 60
catcgtggaa aaagaagacg ttccaaccac gtcttcaaag caagtggatt gatgtgatat 120
ctccactgac gtaagggatg acgcacaatc ccactatcct tcgaggcctc atcgttgaag 180
atgcctctgc cgacagtggt cccaaagatg gacccccacc cacgaggagc atcgtggaaa 240
aagaagacgt tccaaccacg tcttcaaagc aagtggattg atgttatatc tccactgacg 300
taagggatga cgcacaatcc cactatcctt cg 332

<210> SEQ ID NO 6
<211> LENGTH: 524
<212> TYPE: DNA
<213> ORGANISM: Cauliflower mosaic virus

<400> SEQUENCE: 6
ggtccgatgt gagacttttc aacaaagggt aatatccgga aacctcctcg gattccattg 60
cccagctatc tgtcacttta ttgtgaagat agtggaaaag gaaggtggct cctacaaatg 120
ccatcattgc gataaaggaa aggccatcgt tgaagatgcc tctgccgaca gtggtcccaa 180
agatggaccc ccacccacga ggagcatcgt ggaaaaagaa gacgttccaa ccacgtcttc 240
aaagcaagtg gattgatgtg atggtccgat gtgagacttt tcaacaaagg gtaatatccg 300
gaaacctcct cggattccat tgcccagcta tctgtcactt tattgtgaag atagtggaaa 360
aggaaggtgg ctcctacaaa tgccatcatt gcgataaagg aaaggccatc gttgaagatg 420
cctctgccga cagtggtccc aaagatggac ccccacccac gaggagcatc gtggaaaaag 480
aagacgttcc aaccacgtct tcaaagcaag tggattgatg tgat 524

<210> SEQ ID NO 7
<211> LENGTH: 921
<212> TYPE: DNA
<213> ORGANISM: Oryza sativa

<400> SEQUENCE: 7
tcgaggtcat tcatatgctt gagaagagag tcgggatagt ccaaaataaa acaaaggtaa 60
gattacctgg tcaaaagtga aaacatcagt taaaaggtgg tataaagtaa aatatcggta 120
ataaaaggtg gcccaaagtg aaatttactc ttttctacta ttataaaaat tgaggatgtt 180
tttgtcggta ctttgatacg tcatttttgt atgaattggt ttttaagttt attcgctttt 240
ggaaatgcat atctgtattt gagtcgggtt ttaagttcgt ttgcttttgt aaatacagag 300
ggatttgtat aagaaatatc tttagaaaaa cccatatgct aatttgacat aatttttgag 360
aaaaatatat attcaggcga attctcacaa tgaacaataa taagattaaa atagctttcc 420
cccgttgcag cgcatgggta ttttttctag taaaaataaa agataaactt agactcaaaa 480
catttacaaa aacaacccct aaagttccta aagcccaaag tgctatccac gatccatagc 540
aagcccagcc caacccaacc caacccagcc caccccagtc cagccaactg gacaatagtc 600
tccacacccc cccactatca ccgtgagttg tccgcacgca ccgcacgtct cgcagccaaa 660
aaaaaaaaga aagaaaaaaa agaaaaagaa aaaacagcag gtgggtccgg gtcgtggggg 720
ccggaaacgc gaggaggatc gcgagccagc gacgaggccg gccctccctc cgcttccaaa 780
gaaacgcccc ccatcgccac tatatacata cccccccctc tcctcccatc cccccaaccc 840
taccaccacc accaccacca cctccacctc ctcccccctc gctgccggac gacgagctcc 900 tccccccctcc ccctccgccg c 921

<210> SEQ ID NO 8
<211> LENGTH: 1577
<212> TYPE: DNA
<213> ORGANISM: Arabidopsis thaliana

<400> SEQUENCE: 8
taaatgacat cagatacacg cttgtgaacc atctttaaag tattgatgga ctcttcacta 60
tgaaagctct ctttaaaatt aattttcttt gtacatgtct ctaagcaatg tcaaattaat 120
tagaggtcca aattcaaaaa aatgtcgtat tgaatcattc cattactaaa ttggttcaat 180
gtcagattta aacagcctag ggataattta gtgagatatg agattctact ttcaacatat 240
actaatccta aatctctagc aactttttat ataagctata aatatcatga aaatgtattt 300
taatcgtttc ataatttatg cagtcacact aatggaaaaa aggccaatta ttattatttt 360
cttcagacta taaatgaaaa cataaattaa aatgcagatt agtttaaaat tttaataagt 420
aagtaaaatg cttatagcct tatacaaaat catatttgga agtttctaac attgttgcaa 480
tttgttatca caaatcacag taatatttgt atactaatta gtaattacaa ctatacacaa 540
atttaaatgg gtaatcatat atttgtgtcc agtggattga acaaatatgc tcggcccatg 600
cggaagtaat gccaattttg ggtgagtaaa gcccatgcga aattttcaca taagaaatgc 660
atgctttttg ttttcaacga catgagttgc atgcttttta tcattgctta tatagttgca 720
agtttgcaac tccttgatat ttttttatg tagacactac taccaccaaa aacttttggt 780
ctgcttattc ttgtttacta tgtaaaaaaa ataaatgaat tgtttattta ctccgatttg 840
atggagtctg gtttatgagg ttttatagcc tttacagaaa attgatagtt acaaaaatat 900
ttttcaaaaa taaaagggta aaaccgtcat ttcaagttgt tattgttttg ggggactgga 960
tttgaaatga aatatagaac cggaaaaacaa ggtgagccga agtcgaagcc tttggacccg 1020
tttttatatt tactcctccc attcccttct ccttcaatcc ttccttcctc ctcctccctt 1080
cttcttcttc ccctctttca ttttccagcc actacaaact tttctatctc tactttttttt 1140 cctctcgatt tcaggtactt tttgagaccc tttgttgtga ttttcgaaca cacaccccaa 1200
ttacgtttga tttttgatcc cgcatcgatt tcaattcatc cgtttctgag tttcttttgg 1260
atctgggtgt cttgagctaa tcttttcgat ctgttgttta tcgattttac tcatgcgtat 1320
gttcattaca ccatttgtta tttgtttaat caaccaaaag actcatgttt ttcaaatgtc 1380
tttaatataa tttttctgat tgaattttat aatatttaca tgattctgga tccagaatat 1440
ccttcttctt cttccatttt gtcctgtatt gatttgtctt tgaaaaagga ttgttctttg 1500
tatctgtatt ggtgaaaaag gattgttatt tgttgataaa aatttgatct ttaaacaatg 1560
tttggttttg cataaag 1577

<210> SEQ ID NO 9
<211> LENGTH: 1184
<212> TYPE: DNA
<213> ORGANISM: Artificial Sequence
<220> FEATURE:
<223> OTHER INFORMATION: Synthetic promoter sequence

<400> SEQUENCE: 9
aagctagctt gtcgaccatc gttgaagatg cctctgccga cagtggtccc aaagatggac 60

```
ccccacccac ctcgaccatc gttgaagatg cctctgccga cagtggtccc aaagatggac    120

ccccacccac ctcgaccatc gttgaagatg cctctgccga cagtggtccc aaagatggac    180

ccccacccac ctcgaccatc gttgaagatg cctctgccga cagtggtccc aaagatggac    240

ccccacccac ctcgacagct tactcgaggt cattcatatg cttgagaaga gagtcgggat    300

agtccaaaat aaaacaaagg taagattacc tggtcaaaag tgaaaacatc agttaaaagg    360

tggtataaag taaaatatcg gtaataaaag gtggcccaaa gtgaaattta ctcttttcta    420

ctattataaa aattgaggat gtttttgtcg gtactttgat acgtcatttt tgtatgaatt    480

ggtttttaag tttattcgct tttggaaatg catatctgta tttgagtcgg gttttaagtt    540

cgtttgcttt tgtaaataca gagggatttg tataagaaat atctttagaa aaacccatat    600

gctaatttga cataattttt gagaaaaata tatattcagg cgaattctca caatgaacaa    660

taataagatt aaaatagctt tcccccgttg cagcgcatgg gtattttttc tagtaaaaat    720

aaaagataaa cttagactca aaacatttac aaaaacaacc cctaaagttc ctaaagccca    780

aagtgctatc cacgatccat agcaagccca gcccaaccca acccaaccca gcccacccca    840

gtccagccaa ctggacaata gtctccacac ccccccacta tcaccgtgag ttgtccgcac    900

gcaccgcacg tctcgcagcc aaaaaaaaaa agaaagaaaa aaaagaaaaa gaaaaaacag    960

caggtgggtc cgggtcgtgg gggccggaaa cgcgaggagg atcgcgagcc agcgacgagg   1020

ccggccctcc ctccgcttcc aaagaaacgc cccccatcgc cactatatac atacccccccc   1080

ctctcctccc atccccccaa ccctaccacc accaccacca ccacctccac ctcctccccc   1140

ctcgctgccg gacgacgagc tcctcccccc tccccctccg ccgc                    1184
```

<210> SEQ ID NO 10
<211> LENGTH: 1184
<212> TYPE: DNA
<213> ORGANISM: Artificial Sequence
<220> FEATURE:
<223> OTHER INFORMATION: Synthetic promoter sequence

<400> SEQUENCE: 10

```
aagcttactc gaggtcattc atatgcttga gaagagagtc gggatagtcc aaaataaaac     60

aaaggtaaga ttacctggtc aaaagtgaaa acatcagtta aaaggtggta taaagtaaaa    120

tatcggtaat aaaaggtggc ccaaagtgaa atttactctt ttctactatt ataaaaattg    180

aggatgtttt tgtcggtact ttgatacgtc atttttgtat gaattggttt ttaagtttat    240

tcgcttttgg aaatgcatat ctgtatttga gtcgggtttt aagttcgttt gcttttgtaa    300

atacagaggg atttgtataa gaaatatctt tagaaaaacc catatgctaa tttgacataa    360

tttttgagaa aaatatatat tcaggcgaat tagcttgtcg accatcgttg aagatgcctc    420

tgccgacagt ggtcccaaag atggaccccc acccacctcg accatcgttg aagatgcctc    480

tgccgacagt ggtcccaaag atggaccccc acccacctcg accatcgttg aagatgcctc    540

tgccgacagt ggtcccaaag atggaccccc acccacctcg accatcgttg aagatgcctc    600

tgccgacagt ggtcccaaag atggaccccc acccacctcg acaattctca caatgaacaa    660

taataagatt aaaatagctt tcccccgttg cagcgcatgg gtattttttc tagtaaaaat    720

aaaagataaa cttagactca aaacatttac aaaaacaacc cctaaagttc ctaaagccca    780

aagtgctatc cacgatccat agcaagccca gcccaaccca acccaaccca gcccacccca    840

gtccagccaa ctggacaata gtctccacac ccccccacta tcaccgtgag ttgtccgcac    900

gcaccgcacg tctcgcagcc aaaaaaaaaa agaaagaaaa aaaagaaaaa gaaaaaacag    960
```

```
caggtgggtc cgggtcgtgg gggccggaaa cgcgaggagg atcgcgagcc agcgacgagg   1020

ccggccctcc ctccgcttcc aaagaaacgc cccccatcgc cactatatac atacccccccc   1080

ctctcctccc atccccccaa ccctaccacc accaccacca ccacctccac ctcctccccc   1140

ctcgctgccg gacgacgagc tcctcccccc tcccccctccg ccgc                   1184
```

<210> SEQ ID NO 11
<211> LENGTH: 1176
<212> TYPE: DNA
<213> ORGANISM: Artificial Sequence
<220> FEATURE:
<223> OTHER INFORMATION: Synthetic promoter sequence

<400> SEQUENCE: 11

```
aagcttactc gaggtcattc atatgcttga gaagagagtc gggatagtcc aaaataaaac     60

aaaggtaaga ttacctggtc aaaagtgaaa acatcagtta aaaggtggta taaagtaaaa    120

tatcggtaat aaaaggtggc ccaaagtgaa atttactctt ttctactatt ataaaaattg    180

aggatgtttt tgtcggtact ttgatacgtc atttttgtat gaattggttt ttaagtttat    240

tcgcttttgg aaatgcatat ctgtatttga gtcgggtttt aagttcgttt gcttttgtaa    300

atacagaggg atttgtataa gaaatatctt tagaaaaacc catatgctaa tttgacataa    360

tttttgagaa aaatatatat tcaggcgaat tctcacaatg aacaataata agattaaaat    420

agctttcccc cgttgcagcg catgggtatt ttttctagta aaaataaaag ataaacttag    480

actcaaaaca tttacaaaaa caacccctaa agttcctaaa gcccaaagtg ctatccacga    540

tccatagcaa gcccagccca acccaaccca acccagccca ccccagtcca gccaactgga    600

caatagtctc cacacccccc cactatcacc gtgagttgtc cgcacgcacc gcacgtctcg    660

cagccaaaaa aaaaaagaaa gaaaaaaaag aaaaagaaaa aacagcaggt gggtccgggt    720

cgtgggggcc ggaaacgcga ggaggatcgc gagccagcga cgaggagctt gtcgaccatc    780

gttgaagatg cctctgccga cagtggtccc aaagatggac cccccacccac ctcgaccatc    840

gttgaagatg cctctgccga cagtggtccc aaagatggac cccccacccac ctcgaccatc    900

gttgaagatg cctctgccga cagtggtccc aaagatggac cccccacccac ctcgaccatc    960

gttgaagatg cctctgccga cagtggtccc aaagatggac cccccacccac ctcgacccct   1020

ccctccgctt ccaaagaaac gccccccatc gccactatat acatacccccc ccctctcctc   1080

ccatcccccc aaccctacca ccaccaccac caccacctcc acctcctccc ccctcgctgc   1140

cggacgacga gctcctcccc cctcccccctc cgccgc                            1176
```

<210> SEQ ID NO 12
<211> LENGTH: 1158
<212> TYPE: DNA
<213> ORGANISM: Artificial Sequence
<220> FEATURE:
<223> OTHER INFORMATION: Synthetic promoter sequence

<400> SEQUENCE: 12

```
aagctagctt ctgacgtaag ggatgacgca cctgacgtaa gggatgacgc acctgacgta     60

agggatgacg cacctgacgt aagggatgac gcactcgaga tccccatctc cactgacgta    120

agggatgacg cacaatccca ctatccttcg caagaccctt cctctatata aggaagttca    180

tttcatttgg agaggacacg ctgacaagct agcttggctg caggtagatc agcttactcg    240

aggtcattca tatgcttgag aagagagtcg ggatagtcca aaataaaaca aaggtaagat    300

tacctggtca aaagtgaaaa catcagttaa aaggtggtat aaagtaaaat atcggtaata    360
```

```
aaaggtggcc caaagtgaaa tttactcttt tctactatta taaaaattga ggatgttttt    420

gtcggtactt tgatacgtca tttttgtatg aattggtttt taagtttatt cgcttttgga    480

aatgcatatc tgtatttgag tcgggtttta agttcgtttg cttttgtaaa tacagaggga    540

tttgtataag aaatatcttt agaaaaaccc atatgctaat ttgacataat tttgagaaa     600

aatatatatt caggcgaatt ctcacaatga acaataataa gattaaaata gctttccccc    660

gttgcagcgc atgggtattt tttctagtaa aaataaaaga taaacttaga ctcaaaacat    720

ttacaaaaac aaccccctaaa gttcctaaag cccaaagtgc tatccacgat ccatagcaag   780

cccagcccaa cccaacccaa cccagcccac cccagtccag ccaactggac aatagtctcc    840

acaccccccc actatcaccg tgagttgtcc gcacgcaccg cacgtctcgc agccaaaaaa    900

aaaaagaaag aaaaaaaaga aaaagaaaaa acagcaggtg ggtccgggtc gtgggggccg    960

gaaacgcgag gaggatcgcg agccagcgac gaggccggcc ctccctccgc ttccaaagaa   1020

acgcccccca tcgccactat atacataccc ccccctctcc tcccatcccc ccaaccctac   1080

caccaccacc accaccacct ccacctcctc ccccctcgct gccggacgac gagctcctcc   1140

cccctccccc tccgccgc                                                 1158
```

<210> SEQ ID NO 13
<211> LENGTH: 1158
<212> TYPE: DNA
<213> ORGANISM: Artificial Sequence
<220> FEATURE:
<223> OTHER INFORMATION: Synthetic promoter sequence

<400> SEQUENCE: 13

```
aagcttactc gaggtcattc atatgcttga gaagagagtc gggatagtcc aaaataaaac     60

aaaggtaaga ttacctggtc aaaagtgaaa acatcagtta aaggtggta taaagtaaaa     120

tatcggtaat aaaaggtggc ccaaagtgaa atttactctt ttctactatt ataaaaattg    180

aggatgtttt tgtcggtact ttgatacgtc atttttgtat gaattggttt ttaagtttat    240

tcgcttttgg aaatgcatat ctgtatttga gtcgggtttt aagttcgttt gcttttgtaa    300

atacagaggg atttgtataa gaaatatctt tagaaaaacc catatgctaa tttgacataa    360

tttttgagaa aaatatatat tcaggcgaat tagcttctga cgtaagggat gacgcacctg    420

acgtaaggga tgacgcacct gacgtaaggg atgacgcacc tgacgtaagg gatgacgcac    480

tcgagatccc catctccact gacgtaaggg atgacgcaca atcccactat ccttcgcaag    540

acccttcctc tatataagga agttcatttc atttggagag gacacgctga caagctagct    600

tggctgcagg tagatcaatt ctcacaatga acaataataa gattaaaata gctttccccc    660

gttgcagcgc atgggtattt tttctagtaa aaataaaaga taaacttaga ctcaaaacat    720

ttacaaaaac aaccccctaaa gttcctaaag cccaaagtgc tatccacgat ccatagcaag   780

cccagcccaa cccaacccaa cccagcccac cccagtccag ccaactggac aatagtctcc    840

acaccccccc actatcaccg tgagttgtcc gcacgcaccg cacgtctcgc agccaaaaaa    900

aaaaagaaag aaaaaaaaga aaaagaaaaa acagcaggtg ggtccgggtc gtgggggccg    960

gaaacgcgag gaggatcgcg agccagcgac gaggccggcc ctccctccgc ttccaaagaa   1020

acgcccccca tcgccactat atacataccc ccccctctcc tcccatcccc ccaaccctac   1080

caccaccacc accaccacct ccacctcctc ccccctcgct gccggacgac gagctcctcc   1140

cccctccccc tccgccgc                                                 1158
```

<210> SEQ ID NO 14

<211> LENGTH: 1150
<212> TYPE: DNA
<213> ORGANISM: Artificial Sequence
<220> FEATURE:
<223> OTHER INFORMATION: Synthetic promoter sequence

<400> SEQUENCE: 14

```
aagcttactc gaggtcattc atatgcttga gaagagagtc gggatagtcc aaaataaaac     60

aaaggtaaga ttacctggtc aaaagtgaaa acatcagtta aaaggtggta taaagtaaaa    120

tatcggtaat aaaaggtggc ccaaagtgaa atttactctt ttctactatt ataaaaattg    180

aggatgtttt tgtcggtact ttgatacgtc atttttgtat gaattggttt ttaagtttat    240

tcgcttttgg aaatgcatat ctgtatttga gtcgggtttt aagttcgttt gcttttgtaa    300

atacagaggg atttgtataa gaaatatctt tagaaaaacc catatgctaa tttgacataa    360

tttttgagaa aaatatatat tcaggcgaat tctcacaatg aacaataata agattaaaat    420

agctttcccc cgttgcagcg catgggtatt ttttctagta aaaataaaag ataaacttag    480

actcaaaaca tttacaaaaa caacccctaa agttcctaaa gcccaaagtg ctatccacga    540

tccatagcaa gcccagccca acccaaccca acccagccca ccccagtcca gccaactgga    600

caatagtctc cacaccccc cactatcacc gtgagttgtc cgcacgcacc gcacgtctcg    660

cagccaaaaa aaaaaagaaa gaaaaaaaag aaaaagaaaa aacagcaggt gggtccgggt    720

cgtgggggcc ggaaacgcga ggaggatcgc gagccagcga cgaggagctt ctgacgtaag    780

ggatgacgca cctgacgtaa gggatgacgc acctgacgta agggatgacg cacctgacgt    840

aagggatgac gcactcgaga tccccatctc cactgacgta agggatgacg cacaatccca    900

ctatccttcg caagaccctt cctctatata aggaagttca tttcatttgg agaggacacg    960

ctgacaagct agcttggctg caggtagatc cctccctcc gcttccaaag aaacgccccc   1020

catcgccact atatacatac cccccctct cctcccatcc ccccaaccct accaccacca   1080

ccaccaccac ctccacctcc tccccctcg ctgccggacg acgagctcct ccccctccc   1140

cctccgccgc                                                          1150
```

<210> SEQ ID NO 15
<211> LENGTH: 1065
<212> TYPE: DNA
<213> ORGANISM: Artificial Sequence
<220> FEATURE:
<223> OTHER INFORMATION: Synthetic promoter sequence

<400> SEQUENCE: 15

```
aagcttaggc ctcatcgtgg aaaaagaaga cgttccaacc acgtcttcaa agcaagtgga     60

ttgatgtgat aagctcctca tcgtggaaaa agaagacgtt ccaaccacgt cttcaaagca    120

agtggattga tgtgataagc ttactcgagg tcattcatat gcttgagaag agagtcggga    180

tagtccaaaa taaaacaaag gtaagattac ctggtcaaaa gtgaaaacat cagttaaaag    240

gtggtataaa gtaaaatatc ggtaataaaa ggtggcccaa agtgaaattt actcttttct    300

actattataa aaattgagga tgtttttgtc ggtactttga tacgtcattt ttgtatgaat    360

tggtttttaa gtttattcgc ttttggaaat gcatatctgt atttgagtcg ggttttaagt    420

tcgtttgctt ttgtaaatac agagggattt gtataagaaa tatctttaga aaaacccata    480

tgctaatttg acataatttt tgagaaaaat atatattcag gcgaattctc acaatgaaca    540

ataataagat taaaatagct ttcccccgtt gcagcgcatg ggtatttttt ctagtaaaaa    600

taaaagataa acttagactc aaaacattta caaaaacaac ccctaaagtt cctaaagccc    660
```

aaagtgctat ccacgatcca tagcaagccc agcccaaccc aacccaaccc agcccacccc 720
agtccagcca actggacaat agtctccaca cccccccact atcaccgtga gttgtccgca 780
cgcaccgcac gtctcgcagc caaaaaaaaa aagaaagaaa aaaaagaaaa agaaaaaaca 840
gcaggtgggt ccgggtcgtg gggccggaa acgcgaggag gatcgcgagc cagcgacgag 900
gccggccctc cctccgcttc caaagaaacg ccccccatcg ccactatata catacccccc 960
cctctcctcc catcccccca accctaccac caccaccacc accacctcca cctcctcccc 1020
cctcgctgcc ggacgacgag ctcctccccc ctccccctcc gccgc 1065

<210> SEQ ID NO 16
<211> LENGTH: 1073
<212> TYPE: DNA
<213> ORGANISM: Artificial Sequence
<220> FEATURE:
<223> OTHER INFORMATION: Synthetic promoter sequence

<400> SEQUENCE: 16
aagcttactc gaggtcattc atatgcttga gaagagagtc gggatagtcc aaaataaaac 60
aaaggtaaga ttacctggtc aaaagtgaaa acatcagtta aaaggtggta taaagtaaaa 120
tatcggtaat aaaaggtggc ccaaagtgaa atttactctt ttctactatt ataaaaattg 180
aggatgtttt tgtcggtact ttgatacgtc atttttgtat gaattggttt ttaagtttat 240
tcgcttttgg aaatgcatat ctgtatttga gtcgggtttt aagttcgttt gcttttgtaa 300
atacagaggg atttgtataa gaaatatctt tagaaaaacc catatgctaa tttgacataa 360
tttttgagaa aaatatatat tcaggcgaat tagcttaggc ctcatcgtgg aaaaagaaga 420
cgttccaacc acgtcttcaa agcaagtgga ttgatgtgat aagctcctca tcgtggaaaa 480
agaagacgtt ccaaccacgt cttcaaagca agtggattga tgtgataagc taattctcac 540
aatgaacaat aataagatta aaatagcttt cccccgttgc agcgcatggg tattttttct 600
agtaaaaata aaagataaac ttagactcaa aacatttaca aaaacaaccc ctaaagttcc 660
taaagcccaa agtgctatcc acgatccata gcaagcccag cccaacccaa cccaacccag 720
cccaccccag tccagccaac tggacaatag tctccacacc cccccactat caccgtgagt 780
tgtccgcacg caccgcacgt ctcgcagcca aaaaaaaaaa gaaagaaaaa aaagaaaaag 840
aaaaaacagc aggtgggtcc gggtcgtggg ggccggaaac gcgaggagga tcgcgagcca 900
gcgacgaggc cggccctccc tccgcttcca aagaaacgcc ccccatcgcc actatataca 960
tacccccccc tctcctccca tcccccccaac cctaccacca ccaccaccac cacctccacc 1020
tcctcccccc tcgctgccgg acgacgagct cctccccccct cccccctccgc cgc 1073

<210> SEQ ID NO 17
<211> LENGTH: 1065
<212> TYPE: DNA
<213> ORGANISM: Artificial Sequence
<220> FEATURE:
<223> OTHER INFORMATION: Synthetic promoter sequence

<400> SEQUENCE: 17
aagcttactc gaggtcattc atatgcttga gaagagagtc gggatagtcc aaaataaaac 60
aaaggtaaga ttacctggtc aaaagtgaaa acatcagtta aaaggtggta taaagtaaaa 120
tatcggtaat aaaaggtggc ccaaagtgaa atttactctt ttctactatt ataaaaattg 180
aggatgtttt tgtcggtact ttgatacgtc atttttgtat gaattggttt ttaagtttat 240
tcgcttttgg aaatgcatat ctgtatttga gtcgggtttt aagttcgttt gcttttgtaa 300
atacagaggg atttgtataa gaaatatctt tagaaaaacc catatgctaa tttgacataa 360
tttttgagaa aaatatatat tcaggcgaat tctcacaatg aacaataata agattaaaat 420
agctttcccc cgttgcagcg catgggtatt ttttctagta aaaataaaag ataaacttag 480
actcaaaaca tttacaaaaa caacccctaa agttcctaaa gcccaaagtg ctatccacga 540
tccatagcaa gcccagccca acccaaccca acccagccca ccccagtcca gccaactgga 600
caatagtctc cacacccccc cactatcacc gtgagttgtc cgcacgcacc gcacgtctcg 660
cagccaaaaa aaaaaagaaa gaaaaaaaag aaaaagaaaa aacagcaggt gggtccgggt 720
cgtgggggcc ggaaacgcga ggaggatcgc gagccagcga cgaggagctt aggcctcatc 780
gtggaaaaag aagacgttcc aaccacgtct tcaaagcaag tggattgatg tgataagctc 840
ctcatcgtgg aaaaagaaga cgttccaacc acgtcttcaa agcaagtgga ttgatgtgat 900
aagctccctc cctccgcttc caaagaaacg ccccccatcg ccactatata catacccccc 960
cctctcctcc catcccccca accctaccac caccaccacc accacctcca cctcctcccc 1020
cctcgctgcc ggacgacgag ctcctccccc ctccccctcc gccgc 1065

<210> SEQ ID NO 18
<211> LENGTH: 1273
<212> TYPE: DNA
<213> ORGANISM: Artificial Sequence
<220> FEATURE:
<223> OTHER INFORMATION: Synthetic promoter sequence

<400> SEQUENCE: 18
aagcttaggc ctcatcgttg aagatgcctc tgccgacagt ggtcccaaag atggaccccc 60
acccacgagg agcatcgtgg aaaaagaaga cgttccaacc acgtcttcaa agcaagtgga 120
ttgatgtgat atctccactg acgtaaggga tgacgcacaa tcccactatc cttcgaggcc 180
tcatcgttga agatgcctct gccgacagtg gtcccaaaga tggaccccca cccacgagga 240
gcatcgtgga aaaagaagac gttccaacca cgtcttcaaa gcaagtggat tgatgttata 300
tctccactga cgtaagggat gacgcacaat cccactatcc ttcgaagctt actcgaggtc 360
attcatatgc ttgagaagag agtcgggata gtccaaaata aaacaaaggt aagattacct 420
ggtcaaaagt gaaaacatca gttaaaaggt ggtataaagt aaaatatcgg taataaaagg 480
tggcccaaag tgaaatttac tcttttctac tattataaaa attgaggatg tttttgtcgg 540
tactttgata cgtcattttt gtatgaattg gtttttaagt ttattcgctt ttggaaatgc 600
atatctgtat ttgagtcggg ttttaagttc gtttgctttt gtaaatacag agggatttgt 660
ataagaaata tctttagaaa aacccatatg ctaatttgac ataatttttg agaaaaatat 720
atattcaggc gaattctcac aatgaacaat aataagatta aaatagcttt cccccgttgc 780
agcgcatggg tatttttttct agtaaaaata aaagataaac ttagactcaa aacatttaca 840
aaaacaaccc ctaaagttcc taaagcccaa agtgctatcc acgatccata gcaagcccag 900
cccaacccaa cccaacccag cccaccccag tccagccaac tggacaatag tctccacacc 960
cccccactat caccgtgagt tgtccgcacg caccgcacgt ctcgcagcca aaaaaaaaaa 1020
gaaagaaaaa aaagaaaaag aaaaaacagc aggtgggtcc gggtcgtggg ggccggaaac 1080
gcgaggagga tcgcgagcca gcgacgaggc cggccctccc tccgcttcca aagaaacgcc 1140
ccccatcgcc actatataca taccccccc tctcctccca tccccccaac cctaccacca 1200
ccaccaccac cacctccacc tcctcccccc tcgctgccgg acgacgagct cctcccccct 1260
ccccctccgc cgc 1273

<210> SEQ ID NO 19
<211> LENGTH: 1281
<212> TYPE: DNA
<213> ORGANISM: Artificial Sequence
<220> FEATURE:
<223> OTHER INFORMATION: Synthetic promoter sequence

<400> SEQUENCE: 19
aagcttactc gaggtcattc atatgcttga gaagagagtc gggatagtcc aaaataaaac 60
aaaggtaaga ttacctggtc aaaagtgaaa acatcagtta aaaggtggta taaagtaaaa 120
tatcggtaat aaaaggtggc ccaaagtgaa atttactctt ttctactatt ataaaaattg 180
aggatgtttt tgtcggtact ttgatacgtc atttttgtat gaattggttt ttaagtttat 240
tcgcttttgg aaatgcatat ctgtatttga gtcgggtttt aagttcgttt gcttttgtaa 300
atacagaggg atttgtataa gaaatatctt tagaaaaacc catatgctaa tttgacataa 360
tttttgagaa aaatatatat tcaggcgaat tagcttaggc ctcatcgttg aagatgcctc 420
tgccgacagt ggtcccaaag atggaccccc acccacgagg agcatcgtgg aaaaagaaga 480
cgttccaacc acgtcttcaa agcaagtgga ttgatgtgat atctccactg acgtaaggga 540
tgacgcacaa tcccactatc cttcgaggcc tcatcgttga agatgcctct gccgacagtg 600
gtcccaaaga tggaccccca cccacgagga gcatcgtgga aaaagaagac gttccaacca 660
cgtcttcaaa gcaagtggat tgatgttata tctccactga cgtaagggat gacgcacaat 720
cccactatcc ttcgaagcta attctcacaa tgaacaataa taagattaaa atagctttcc 780
cccgttgcag cgcatgggta ttttttctag taaaaataaa agataaactt agactcaaaa 840
catttacaaa aacaacccct aaagttccta aagcccaaag tgctatccac gatccatagc 900
aagcccagcc caacccaacc caacccagcc caccccagtc cagccaactg gacaatagtc 960
tccacacccc cccactatca ccgtgagttg tccgcacgca ccgcacgtct cgcagccaaa 1020
aaaaaaaaga aagaaaaaaa agaaaaagaa aaaacagcag gtgggtccgg gtcgtggggg 1080
ccggaaacgc gaggaggatc gcgagccagc gacgaggccg gccctccctc cgcttccaaa 1140
gaaacgcccc ccatcgccac tatatacata cccccccctc tcctcccatc cccccaaccc 1200
taccaccacc accaccacca cctccacctc ctcccccctc gctgccggac gacgagctcc 1260 tccccccctcc ccctccgccg c 1281

<210> SEQ ID NO 20
<211> LENGTH: 1273
<212> TYPE: DNA
<213> ORGANISM: Artificial Sequence
<220> FEATURE:
<223> OTHER INFORMATION: Synthetic promoter sequence

<400> SEQUENCE: 20
aagcttactc gaggtcattc atatgcttga gaagagagtc gggatagtcc aaaataaaac 60
aaaggtaaga ttacctggtc aaaagtgaaa acatcagtta aaaggtggta taaagtaaaa 120
tatcggtaat aaaaggtggc ccaaagtgaa atttactctt ttctactatt ataaaaattg 180
aggatgtttt tgtcggtact ttgatacgtc atttttgtat gaattggttt ttaagtttat 240
tcgcttttgg aaatgcatat ctgtatttga gtcgggtttt aagttcgttt gcttttgtaa 300
atacagaggg atttgtataa gaaatatctt tagaaaaacc catatgctaa tttgacataa 360
tttttgagaa aaatatatat tcaggcgaat tctcacaatg aacaataata agattaaaat 420
agctttcccc cgttgcagcg catgggtatt ttttctagta aaaataaaag ataaacttag 480

-continued

```
actcaaaaca tttacaaaaa caacccctaa agttcctaaa gcccaaagtg ctatccacga    540
tccatagcaa gcccagccca acccaaccca acccagccca ccccagtcca gccaactgga    600
caatagtctc cacacccccc cactatcacc gtgagttgtc cgcacgcacc gcacgtctcg    660
cagccaaaaa aaaaaagaaa gaaaaaaaag aaaaagaaaa aacagcaggt gggtccgggt    720
cgtgggggcc ggaaacgcga ggaggatcgc gagccagcga cgaggagctt aggcctcatc    780
gttgaagatg cctctgccga cagtggtccc aaagatggac ccccacccac gaggagcatc    840
gtggaaaaag aagacgttcc aaccacgtct tcaaagcaag tggattgatg tgatatctcc    900
actgacgtaa gggatgacgc acaatcccac tatccttcga ggcctcatcg ttgaagatgc    960
ctctgccgac agtggtccca aagatggacc cccacccacg aggagcatcg tggaaaaaga   1020
agacgttcca accacgtctt caaagcaagt ggattgatgt tatatctcca ctgacgtaag   1080
ggatgacgca caatcccact atccttcgaa gctccctccc tccgcttcca aagaaacgcc   1140
ccccatcgcc actatataca tacccccccc tctcctccca tccccccaac cctaccacca   1200
ccaccaccac cacctccacc tcctcccccc tcgctgccgg acgacgagct cctccccccct   1260
ccccctccgc cgc                                                      1273
```

<210> SEQ ID NO 21
<211> LENGTH: 1467
<212> TYPE: DNA
<213> ORGANISM: Artificial Sequence
<220> FEATURE:
<223> OTHER INFORMATION: Synthetic promoter sequence

<400> SEQUENCE: 21

```
aagctagctt ctgcaggtcc gatgtgagac ttttcaacaa agggtaatat ccggaaacct     60
cctcggattc cattgcccag ctatctgtca ctttattgtg aagatagtgg aaaaggaagg    120
tggctcctac aaatgccatc attgcgataa aggaaaggcc atcgttgaag atgcctctgc    180
cgacagtggt cccaaagatg gacccccacc cacgaggagc atcgtggaaa aagaagacgt    240
tccaaccacg tcttcaaagc aagtggattg atgtgatggt ccgatgtgag acttttcaac    300
aaagggtaat atccggaaac ctcctcggat tccattgccc agctatctgt cactttattg    360
tgaagatagt ggaaaaggaa ggtggctcct acaaatgcca tcattgcgat aaaggaaagg    420
ccatcgttga agatgcctct gccgacagtg gtcccaaaga tggaccccca cccacgagga    480
gcatcgtgga aaaagaagac gttccaacca cgtcttcaaa gcaagtggat tgatgtgata    540
gcttactcga ggtcattcat atgcttgaga agagagtcgg gatagtccaa aataaaacaa    600
aggtaagatt acctggtcaa aagtgaaaac atcagttaaa aggtggtata aagtaaaata    660
tcggtaataa aaggtggccc aaagtgaaat ttactctttt ctactattat aaaaattgag    720
gatgtttttg tcggtacttt gatacgtcat ttttgtatga attggttttt aagtttattc    780
gcttttggaa atgcatatct gtatttgagt cgggttttaa gttcgtttgc ttttgtaaat    840
acagagggat ttgtataaga aatatcttta gaaaaaccca tatgctaatt tgacataatt    900
tttgagaaaa atatatattc aggcgaattc tcacaatgaa caataataag attaaaatag    960
ctttcccccg ttgcagcgca tgggtatttt ttctagtaaa aataaaagat aaacttagac   1020
tcaaaacatt tacaaaaaca acccctaaag ttcctaaagc ccaaagtgct atccacgatc   1080
catagcaagc ccagcccaac ccaacccaac ccagcccacc ccagtccagc caactggaca   1140
atagtctcca caccccccca ctatcaccgt gagttgtccg cacgcaccgc acgtctcgca   1200
gccaaaaaaa aaaagaaaga aaaaaaagaa aaagaaaaaa cagcaggtgg gtccgggtcg   1260
```

```
tgggggccgg aaacgcgagg aggatcgcga gccagcgacg aggccggccc tccctccgct   1320

tccaaagaaa cgccccccat cgccactata tacatacccc cccctctcct cccatccccc   1380

caaccctacc accaccacca ccaccacctc cacctcctcc cccctcgctg ccggacgacg   1440

agctcctccc ccctccccct ccgccgc                                       1467
```

```
<210> SEQ ID NO 22
<211> LENGTH: 1467
<212> TYPE: DNA
<213> ORGANISM: Artificial Sequence
<220> FEATURE:
<223> OTHER INFORMATION: Synthetic promoter sequence

<400> SEQUENCE: 22

aagcttactc gaggtcattc atatgcttga gaagagagtc gggatagtcc aaaataaaac     60

aaaggtaaga ttacctggtc aaaagtgaaa acatcagtta aaaggtggta taaagtaaaa    120

tatcggtaat aaaaggtggc ccaaagtgaa atttactctt ttctactatt ataaaaattg    180

aggatgtttt tgtcggtact ttgatacgtc atttttgtat gaattggttt ttaagtttat    240

tcgcttttgg aaatgcatat ctgtatttga gtcgggtttt aagttcgttt gcttttgtaa    300

atacagaggg atttgtataa gaaatatctt tagaaaaacc catatgctaa tttgacataa    360

tttttgagaa aaatatatat tcaggcgaat tagcttctgc aggtccgatg tgagactttt    420

caacaaaggg taatatccgg aaacctcctc ggattccatt gcccagctat ctgtcacttt    480

attgtgaaga tagtggaaaa ggaaggtggc tcctacaaat gccatcattg cgataaagga    540

aaggccatcg ttgaagatgc ctctgccgac agtggtccca aagatggacc cccacccacg    600

aggagcatcg tggaaaaaga agacgttcca accacgtctt caaagcaagt ggattgatgt    660

gatggtccga tgtgagactt ttcaacaaag ggtaatatcc ggaaacctcc tcggattcca    720

ttgcccagct atctgtcact ttattgtgaa gatagtggaa aaggaaggtg gctcctacaa    780

atgccatcat tgcgataaag gaaaggccat cgttgaagat gcctctgccg acagtggtcc    840

caaagatgga cccccaccca cgaggagcat cgtggaaaaa gaagacgttc caaccacgtc    900

ttcaaagcaa gtggattgat gtgataattc tcacaatgaa caataataag attaaaatag    960

ctttccccccg ttgcagcgca tgggtatttt ttctagtaaa aataaaagat aaacttagac   1020

tcaaaacatt tacaaaaaca acccctaaag ttcctaaagc ccaaagtgct atccacgatc   1080

catagcaagc ccagcccaac ccaacccaac ccagcccacc ccagtccagc caactggaca   1140

atagtctcca caccccccca ctatcaccgt gagttgtccg cacgcaccgc acgtctcgca   1200

gccaaaaaaa aaaagaaaga aaaaaaagaa aaagaaaaaa cagcaggtgg gtccgggtcg   1260

tgggggccgg aaacgcgagg aggatcgcga gccagcgacg aggccggccc tccctccgct   1320

tccaaagaaa cgccccccat cgccactata tacatacccc cccctctcct cccatccccc   1380

caaccctacc accaccacca ccaccacctc cacctcctcc cccctcgctg ccggacgacg   1440

agctcctccc ccctccccct ccgccgc                                       1467
```

```
<210> SEQ ID NO 23
<211> LENGTH: 1459
<212> TYPE: DNA
<213> ORGANISM: Artificial Sequence
<220> FEATURE:
<223> OTHER INFORMATION: Artificial promoter sequence

<400> SEQUENCE: 23

aagcttactc gaggtcattc atatgcttga gaagagagtc gggatagtcc aaaataaaac     60
```

```
aaaggtaaga ttacctggtc aaaagtgaaa acatcagtta aaaggtggta taaagtaaaa    120

tatcggtaat aaaaggtggc ccaaagtgaa atttactctt ttctactatt ataaaaattg    180

aggatgtttt tgtcggtact ttgatacgtc atttttgtat gaattggttt ttaagtttat    240

tcgcttttgg aaatgcatat ctgtatttga gtcgggtttt aagttcgttt gcttttgtaa    300

atacagaggg atttgtataa gaaatatctt tagaaaaacc catatgctaa tttgacataa    360

tttttgagaa aaatatatat tcaggcgaat tctcacaatg aacaataata agattaaaat    420

agctttcccc cgttgcagcg catgggtatt ttttctagta aaaataaaag ataaacttag    480

actcaaaaca tttacaaaaa caacccctaa agttcctaaa gcccaaagtg ctatccacga    540

tccatagcaa gcccagccca acccaaccca acccagccca ccccagtcca gccaactgga    600

caatagtctc cacacccccc cactatcacc gtgagttgtc cgcacgcacc gcacgtctcg    660

cagccaaaaa aaaaaagaaa gaaaaaaaag aaaaagaaaa aacagcaggt gggtccgggt    720

cgtgggggcc ggaaacgcga ggaggatcgc gagccagcga cgaggagctt ctgcaggtcc    780

gatgtgagac ttttcaacaa agggtaatat ccggaaacct cctcggattc cattgcccag    840

ctatctgtca ctttattgtg aagatagtgg aaaaggaagg tggctcctac aaatgccatc    900

attgcgataa aggaaaggcc atcgttgaag atgcctctgc cgacagtggt cccaaagatg    960

gacccccacc cacgaggagc atcgtggaaa aagaagacgt tccaaccacg tcttcaaagc   1020

aagtggattg atgtgatggt ccgatgtgag acttttcaac aaagggtaat atccggaaac   1080

ctcctcggat tccattgccc agctatctgt cactttattg tgaagatagt ggaaaaggaa   1140

ggtggctcct acaaatgcca tcattgcgat aaaggaaagg ccatcgttga agatgcctct   1200

gccgacagtg gtcccaaaga tggaccccca cccacgagga gcatcgtgga aaaagaagac   1260

gttccaacca cgtcttcaaa gcaagtggat tgatgtgatc cctccctccg cttccaaaga   1320

aacgcccccc atcgccacta tatacatacc ccccctctc ctcccatccc cccaacccta    1380

ccaccaccac caccaccacc tccacctcct ccccccctcgc tgccggacga cgagctcctc   1440

ccccctcccc ctccgccgc                                                 1459
```

<210> SEQ ID NO 24
<211> LENGTH: 1939
<212> TYPE: DNA
<213> ORGANISM: Artificial Sequence
<220> FEATURE:
<223> OTHER INFORMATION: Synthetic promoter sequence

<400> SEQUENCE: 24

```
taaatgacat cagatacacg cttgtgaacc atctttaaag tattgatgga ctcttcacta     60

tgaaagctct ctttaaaatt aattttcttt gtacatgtct ctaagcaatg tcaaattaat    120

tagaggtcca aattcaaaaa aatgtcgtat tgaatcattc cattactaaa ttggttcaat    180

gtcagattta aacagcctag agcttaggcc tcatcgttga agatgcctct gccgacagtg    240

gtcccaaaga tggaccccca cccacgagga gcatcgtgga aaaagaagac gttccaacca    300

cgtcttcaaa gcaagtggat tgatgtgata tctccactga cgtaagggat gacgcacaat    360

cccactatcc ttcgaggcct catcgttgaa gatgcctctg ccgacagtgg tcccaaagat    420

ggacccccac ccacgaggag catcgtggaa aaagaagacg ttccaaccac gtcttcaaag    480

caagtggatt gatgttatat ctccactgac gtaagggatg acgcacaatc ccactatcct    540

tcgaagctct agggataatt tagtgagata tgagattcta ctttcaacat atactaatcc    600

taaatctcta gcaacttttt atataagcta taaatatcat gaaaatgtat tttaatcgtt    660
```

```
tcataattta tgcagtcaca ctaatggaaa aaaggccaat tattattatt ttcttcagac    720
tataaatgaa aacataaatt aaaatgcaga ttagtttaaa attttaataa gtaagtaaaa    780
tgcttatagc cttatacaaa atcatatttg gaagtttcta acattgttgc aatttgttat    840
cacaaatcac agtaatattt gtatactaat tagtaattac aactatacac aaatttaaat    900
gggtaatcat atatttgtgt ccagtggatt gaacaaatat gctcggccca tgcggaagta    960
atgccaattt tgggtgagta aagcccatgc gaaattttca cataagaaat gcatgctttt   1020
tgttttcaac gacatgagtt gcatgctttt tatcattgct tatatagttg caagtttgca   1080
actccttgat attttttta tgtagacact actaccacca aaaacttttg gtctgcttat   1140
tcttgtttac tatgtaaaaa aaataaatga attgtttatt tactccgatt tgatggagtc   1200
tggtttatga ggttttatag cctttacaga aaattgatag ttacaaaaat atttttcaaa   1260
aataaaaggg taaaaccgtc atttcaagtt gttattgttt tgggggactg gatttgaaat   1320
gaaatataga accggaaaac aaggtgagcc gaagtcgaag cctttggacc cgtttttata   1380
tttactcctc ccattccctt ctccttcaat ccttccttcc tcctcctccc ttcttcttct   1440
tcccctcttt cattttccag ccactacaaa cttttctatc tctacttttt ttcctctcga   1500
tttcaggtac tttttgagac cctttgttgt gattttcgaa cacacacccc aattacgttt   1560
gatttttgat cccgcatcga tttcaattca tccgtttctg agtttctttt ggatctgggt   1620
gtcttgagct aatcttttcg atctgttgtt tatcgatttt actcatgcgt atgttcatta   1680
caccatttgt tatttgttta atcaaccaaa agactcatgt tttcaaatg  tctttaatat   1740
aatttttctg attgaatttt ataatattta catgattctg gatccagaat atccttcttc   1800
ttcttccatt ttgtcctgta ttgatttgtc tttgaaaaag gattgttctt tgtatctgta   1860
ttggtgaaaa aggattgtta tttgttgata aaaatttgat ctttaaacaa tgtttggttt   1920
tgcataaagg tagaagacc                                                 1939
```

<210> SEQ ID NO 25
<211> LENGTH: 1935
<212> TYPE: DNA
<213> ORGANISM: Artificial Sequence
<220> FEATURE:
<223> OTHER INFORMATION: Synthetic promoter sequence

<400> SEQUENCE: 25

```
taaatgacat cagatacacg cttgtgaacc atctttaaag tattgatgga ctcttcacta     60
tgaaagctct ctttaaaatt aattttcttt gtacatgtct ctaagcaatg tcaaattaat    120
tagaggtcca aattcaaaaa aatgtcgtat tgaatcattc cattactaaa ttggttcaat    180
gtcagattta aacagcctag ggataattta gtgagatatg agattctact ttcaacatat    240
actaatccta aatctctagc aactttttat ataagctata aatatcatga aaatgtattt    300
taatcgtttc ataatttatg cagtcacact aatggaaaaa aggccaatta ttattatttt    360
cttcagacta taaatgaaaa cataaattaa aatgcagatt agtttaaaat tttaataagt    420
aagtaaaatg cttatagcct tatacaaaat catatttgga agtttctaac attgttgcaa    480
tttgttatca caaatcacag taatatttgt aagcttaggc ctcatcgttg aagatgcctc    540
tgccgacagt ggtcccaaag atggaccccc acccacgagg agcatcgtgg aaaaagaaga    600
cgttccaacc acgtcttcaa agcaagtgga ttgatgtgat atctccactg acgtaaggga    660
tgacgcacaa tcccactatc cttcgaggcc tcatcgttga agatgcctct gccgacagtg    720
gtcccaaaga tggaccccca cccacgagga gcatcgtgga aaaagaagac gttccaacca    780
```

```
cgtcttcaaa gcaagtggat tgatgttata tctccactga cgtaagggat gacgcacaat    840

cccactatcc ttcgaagctt actaattagt aattacaact atacacaaat ttaaatgggt    900

aatcatatat ttgtgtccag tggattgaac aaatatgctc ggcccatgcg gaagtaatgc    960

caattttggg tgagtaaagc ccatgcgaaa ttttcacata agaaatgcat gctttttgtt   1020

ttcaacgaca tgagttgcat gctttttatc attgcttata tagttgcaag tttgcaactc   1080

cttgatattt tttttatgta gacactacta ccaccaaaaa cttttggtct gcttattctt   1140

gtttactatg taaaaaaaat aaatgaattg tttatttact ccgatttgat ggagtctggt   1200

ttatgaggtt ttatagcctt tacagaaaat tgatagttac aaaaatattt ttcaaaaata   1260

aaagggtaaa accgtcattt caagttgtta ttgttttggg ggactggatt tgaaatgaaa   1320

tatagaaccg gaaaacaagg tgagccgaag tcgaagcctt tggacccgtt tttatattta   1380

ctcctcccat tcccttctcc ttcaatcctt ccttcctcct cctcccttct tcttcttccc   1440

ctctttcatt ttccagccac tacaaacttt tctatctcta cttttttttcc tctcgatttc   1500

aggtactttt tgagaccctt tgttgtgatt ttcgaacaca caccccaatt acgtttgatt   1560

tttgatcccg catcgatttc aattcatccg tttctgagtt tcttttggat ctgggtgtct   1620

tgagctaatc ttttcgatct gttgtttatc gattttactc atgcgtatgt tcattacacc   1680

atttgttatt tgtttaatca accaaaagac tcatgttttt caaatgtctt taatataatt   1740

tttctgattg aattttataa tatttacatg attctggatc cagaatatcc ttcttcttct   1800

tccattttgt cctgtattga tttgtctttg aaaaaggatt gttctttgta tctgtattgg   1860

tgaaaaagga ttgttatttg ttgataaaaa tttgatcttt aaacaatgtt tggttttgca   1920

taaaggtaga agacc                                                    1935
```

<210> SEQ ID NO 26
<211> LENGTH: 1935
<212> TYPE: DNA
<213> ORGANISM: Artificial Sequence
<220> FEATURE:
<223> OTHER INFORMATION: Synthetic promoter sequence

<400> SEQUENCE: 26

```
taaatgacat cagatacacg cttgtgaacc atctttaaag tattgatgga ctcttcacta     60

tgaaagctct ctttaaaatt aattttcttt gtacatgtct ctaagcaatg tcaaattaat    120

tagaggtcca aattcaaaaa aatgtcgtat tgaatcattc cattactaaa ttggttcaat    180

gtcagattta aacagcctag ggataattta gtgagatatg agattctact ttcaacatat    240

actaatccta aatctctagc aactttttat ataagctata aatatcatga aaatgtattt    300

taatcgtttc ataatttatg cagtcacact aatggaaaaa aggccaatta ttattatttt    360

cttcagacta taaatgaaaa cataaattaa aatgcagatt agtttaaaat tttaataagt    420

aagtaaaatg cttatagcct tatacaaaat catatttgga agtttctaac attgttgcaa    480

tttgttatca caaatcacag taatatttgt aagcttcgaa ggatagtggg attgtgcgtc    540

atcccttacg tcagtggaga tataacatca atccacttgc tttgaagacg tggttggaac    600

gtcttctttt tccacgatgc tcctcgtggg tgggggtcca tctttgggac cactgtcggc    660

agaggcatct tcaacgatga ggcctcgaag gatagtggga ttgtgcgtca tcccttacgt    720

cagtggagat atcacatcaa tccacttgct ttgaagacgt ggttggaacg tcttcttttt    780

ccacgatgct cctcgtgggt gggggtccat ctttgggacc actgtcggca gaggcatctt    840

caacgatgag gcctaagctt actaattagt aattacaact atacacaaat ttaaatgggt    900
```

```
aatcatatat ttgtgtccag tggattgaac aaatatgctc ggcccatgcg gaagtaatgc    960

caattttggg tgagtaaagc ccatgcgaaa ttttcacata agaaatgcat gctttttgtt   1020

ttcaacgaca tgagttgcat gctttttatc attgcttata tagttgcaag tttgcaactc   1080

cttgatattt tttttatgta gacactacta ccaccaaaaa cttttggtct gcttattctt   1140

gtttactatg taaaaaaaat aaatgaattg tttatttact ccgatttgat ggagtctggt   1200

ttatgaggtt ttatagcctt tacagaaaat tgatagttac aaaaatattt ttcaaaaata   1260

aaagggtaaa accgtcattt caagttgtta ttgttttggg ggactggatt tgaaatgaaa   1320

tatagaaccg gaaaacaagg tgagccgaag tcgaagcctt tggacccgtt tttatattta   1380

ctcctcccat tcccttctcc ttcaatcctt ccttcctcct cctcccttct tcttcttccc   1440

ctctttcatt ttccagccac tacaaacttt tctatctcta cttttttttcc tctcgatttc   1500

aggtactttt tgagaccctt tgttgtgatt ttcgaacaca caccccaatt acgtttgatt   1560

tttgatcccg catcgatttc aattcatccg tttctgagtt tcttttggat ctgggtgtct   1620

tgagctaatc ttttcgatct gttgtttatc gattttactc atgcgtatgt tcattacacc   1680

atttgttatt tgtttaatca accaaaagac tcatgttttt caaatgtctt taatataatt   1740

tttctgattg aattttataa tatttacatg attctggatc cagaatatcc ttcttcttct   1800

tccattttgt cctgtattga tttgtctttg aaaaaggatt gttctttgta tctgtattgg   1860

tgaaaaagga ttgttatttg ttgataaaaa tttgatcttt aaacaatgtt tggttttgca   1920

taaaggtaga agacc                                                    1935
```

<210> SEQ ID NO 27
<211> LENGTH: 1963
<212> TYPE: DNA
<213> ORGANISM: Artificial Sequence
<220> FEATURE:
<223> OTHER INFORMATION: Synthetic promoter sequence

<400> SEQUENCE: 27

```
ggccgcctgc aggaagctgt accccccaag cttaaatgac atcagataca cgcttgtgaa     60

ccatctttaa agtattgatg gactcttcac tatgaaagct ctctttaaaa ttaattttct    120

ttgtacatgt ctctaagcaa tgtcaaatta attagaggtc caaattcaaa aaaatgtcgt    180

attgaatcat tccattacta aattggttca atgtcagatt taaacagcct agggataatt    240

tagtgagata tgagattcta ctttcaacat atactaatcc taaatctcta gcaacttttt    300

atataagcta taaatatcat gaaaatgtat tttaatcgtt tcataattta tgcagtcaca    360

ctaatggaaa aaaggccaat tattattatt ttcttcagac tataaatgaa aacataaatt    420

aaaatgcaga ttagtttaaa attttaataa gtaagtaaaa tgcttatagc cttatacaaa    480

atcatatttg gaagtttcta acattgttgc aatttgttat cacaaatcac agtaatattt    540

gtatactaat tagtaattac aactatacac aaatttaaat gggtaatcat atatttgtgt    600

ccagtggatt gaacaaatat gctcggccca tgcggaagta atgccaattt tgggtgagta    660

aagcccatgc gaaattttca cataagaaaa gcttaggcct catcgttgaa gatgcctctg    720

ccgacagtgg tcccaaagat ggacccccac ccacgaggag catcgtggaa aaagaagacg    780

ttccaaccac gtcttcaaag caagtggatt gatgtgatat ctccactgac gtaagggatg    840

acgcacaatc ccactatcct tcgaggcctc atcgttgaag atgcctctgc cgacagtggt    900

cccaaagatg gacccccacc cacgaggagc atcgtggaaa aagaagacgt tccaaccacg    960

tcttcaaagc aagtggattg atgttatatc tccactgacg taagggatga cgcacaatcc   1020
```

-continued

```
cactatcctt cgaagcttgc tttttgtttt caacgacatg agttgcatgc tttttatcat   1080

tgcttatata gttgcaagtt tgcaactcct tgatattttt tttatgtaga cactactacc   1140

accaaaaact tttggtctgc ttattcttgt ttactatgta aaaaaaataa atgaattgtt   1200

tatttactcc gatttgatgg agtctggttt atgaggtttt atagccttta cagaaaattg   1260

atagttacaa aaatattttt caaaaataaa agggtaaaac cgtcatttca agttgttatt   1320

gttttggggg actggatttg aaatgaaata tagaaccgga aaacaaggtg agccgaagtc   1380

gaagcctttg gacccgtttt tatatttact cctcccattc ccttctcctt caatccttcc   1440

ttcctcctcc tcccttcttc ttcttcccct ctttcatttt ccagccacta caaacttttc   1500

tatctctact ttttttcctc tcgatttcag gtactttttg agaccctttg ttgtgatttt   1560

cgaacacaca ccccaattac gtttgatttt tgatcccgca tcgatttcaa ttcatccgtt   1620

tctgagtttc ttttggatct gggtgtcttg agctaatctt ttcgatctgt tgtttatcga   1680

ttttactcat gcgtatgttc attacaccat ttgttatttg tttaatcaac caaaagactc   1740

atgtttttca aatgtcttta atataatttt tctgattgaa ttttataata tttacatgat   1800

tctggatcca gaatatcctt cttcttcttc cattttgtcc tgtattgatt tgtctttgaa   1860

aaaggattgt tctttgtatc tgtattggtg aaaaaggatt gttatttgtt gataaaaatt   1920

tgatctttaa acaatgtttg gttttgcata aaggtagaag acc                      1963
```

```
<210> SEQ ID NO 28
<211> LENGTH: 1963
<212> TYPE: DNA
<213> ORGANISM: Artificial Sequence
<220> FEATURE:
<223> OTHER INFORMATION: Synthetic promoter sequence

<400> SEQUENCE: 28

ggccgcctgc aggaagctgt accccccaag cttaaatgac atcagataca cgcttgtgaa     60

ccatctttaa agtattgatg gactcttcac tatgaaagct ctctttaaaa ttaattttct    120

ttgtacatgt ctctaagcaa tgtcaaatta attagaggtc caaattcaaa aaaatgtcgt    180

attgaatcat tccattacta aattggttca atgtcagatt taaacagcct agggataatt    240

tagtgagata tgagattcta ctttcaacat atactaatcc taaatctcta gcaacttttt    300

atataagcta taaatatcat gaaaatgtat tttaatcgtt tcataattta tgcagtcaca    360

ctaatggaaa aaaggccaat tattattatt ttcttcagac tataaatgaa aacataaatt    420

aaaatgcaga ttagtttaaa attttaataa gtaagtaaaa tgcttatagc cttatacaaa    480

atcatatttg gaagtttcta acattgttgc aatttgttat cacaaatcac agtaatattt    540

gtatactaat tagtaattac aactatacac aaatttaaat gggtaatcat atatttgtgt    600

ccagtggatt gaacaaatat gctcggccca tgcggaagta atgccaattt tgggtgagta    660

aagcccatgc gaaattttca cataagaaaa gcttcgaagg atagtgggat tgtgcgtcat    720

cccttacgtc agtggagata taacatcaat ccacttgctt tgaagacgtg gttggaacgt    780

cttctttttc cacgatgctc ctcgtgggtg ggggtccatc tttgggacca ctgtcggcag    840

aggcatcttc aacgatgagg cctcgaagga tagtgggatt gtgcgtcatc ccttacgtca    900

gtggagatat cacatcaatc cacttgcttt gaagacgtgg ttggaacgtc ttctttttcc    960

acgatgctcc tcgtgggtgg gggtccatct ttgggaccac tgtcggcaga ggcatcttca   1020

acgatgaggc ctaagcttgc tttttgtttt caacgacatg agttgcatgc tttttatcat   1080

tgcttatata gttgcaagtt tgcaactcct tgatattttt tttatgtaga cactactacc   1140
```

```
accaaaaact tttggtctgc ttattcttgt ttactatgta aaaaaaataa atgaattgtt   1200

tatttactcc gatttgatgg agtctggttt atgaggtttt atagccttta cagaaaattg   1260

atagttacaa aaatattttt caaaaataaa agggtaaaac cgtcatttca agttgttatt   1320

gttttggggg actggatttg aaatgaaata tagaaccgga aaacaaggtg agccgaagtc   1380

gaagcctttg gacccgtttt tatatttact cctcccattc ccttctcctt caatccttcc   1440

ttcctcctcc tcccttcttc ttcttcccct ctttcatttt ccagccacta caaacttttc   1500

tatctctact ttttttcctc tcgatttcag gtactttttg agaccctttg ttgtgatttt   1560

cgaacacaca ccccaattac gtttgatttt tgatcccgca tcgatttcaa ttcatccgtt   1620

tctgagtttc ttttggatct gggtgtcttg agctaatctt ttcgatctgt tgtttatcga   1680

ttttactcat gcgtatgttc attacaccat ttgttatttg tttaatcaac caaaagactc   1740

atgtttttca aatgtcttta atataatttt tctgattgaa ttttataata tttacatgat   1800

tctggatcca gaatatcctt cttcttcttc cattttgtcc tgtattgatt tgtctttgaa   1860

aaaggattgt tctttgtatc tgtattggtg aaaaaggatt gttatttgtt gataaaaatt   1920

tgatctttaa acaatgtttg gttttgcata aaggtagaag acc                     1963
```

<210> SEQ ID NO 29
<211> LENGTH: 1971
<212> TYPE: DNA
<213> ORGANISM: Artificial Sequence
<220> FEATURE:
<223> OTHER INFORMATION: Synthetic promoter sequence

<400> SEQUENCE: 29

```
ggccgcctgc aggaagctgt acccccccaag cttaaatgac atcagataca cgcttgtgaa     60

ccatctttaa agtattgatg gactcttcac tatgaaagct ctctttaaaa ttaattttct    120

ttgtacatgt ctctaagcaa tgtcaaatta attagaggtc caaattcaaa aaaatgtcgt    180

attgaatcat tccattacta aattggttca atgtcagatt taaacagcct agggataatt    240

tagtgagata tgagattcta ctttcaacat atactaatcc taaatctcta gcaacttttt    300

atataagcta taaatatcat gaaaatgtat tttaatcgtt tcataattta tgcagtcaca    360

ctaatggaaa aaaggccaat tattattatt ttcttcagac tataaatgaa aacataaatt    420

aaaatgcaga ttagtttaaa attttaataa gtaagtaaaa tgcttatagc cttatacaaa    480

atcatatttg gaagtttcta acattgttgc aatttgttat cacaaatcac agtaatattt    540

gtatactaat tagtaattac aactatacac aaatttaaat gggtaatcat atatttgtgt    600

ccagtggatt gaacaaatat gctcggccca tgcggaagta atgccaattt tgggtgagta    660

aagcccatgc gaaattttca cataagaaat gcatgctttt tgttttcaac gacatgagtt    720

gcatgctttt tatcattgct tatatagttg caagtttgca actccttgat attttttta    780

tgtagacact actaccacca aaaacttttg gtctgcttat tcttgtttac tatgtaaaaa    840

aaataaatga attgtttatt tactccgatt tgatggagtc tggtttatga ggttttatag    900

cctttacaga aaattgatag ttacaaaaat atttttcaaa aataaaaggg taaaaccgtc    960

atttcaagtt gttattgttt tgggggactg gatttgaaat gaagcttagg cctcatcgtt   1020

gaagatgcct ctgccgacag tggtcccaaa gatggacccc cacccacgag gagcatcgtg   1080

gaaaaagaag acgttccaac cacgtcttca aagcaagtgg attgatgtga tatctccact   1140

gacgtaaggg atgacgcaca atcccactat ccttcgaggc ctcatcgttg aagatgcctc   1200

tgccgacagt ggtcccaaag atggaccccc acccacgagg agcatcgtgg aaaaagaaga   1260
```

```
cgttccaacc acgtcttcaa agcaagtgga ttgatgttat atctccactg acgtaaggga   1320

tgacgcacaa tcccactatc cttcgaagct atgaaatata gaaccggaaa acaaggtgag   1380

ccgaagtcga agcctttgga cccgttttta tatttactcc tcccattccc ttctccttca   1440

atccttcctt cctcctcctc ccttcttctt cttcccctct ttcattttcc agccactaca   1500

aacttttcta tctctacttt ttttcctctc gatttcaggt actttttgag accctttgtt   1560

gtgattttcg aacacacacc ccaattacgt ttgatttttg atcccgcatc gatttcaatt   1620

catccgtttc tgagtttctt ttggatctgg gtgtcttgag ctaatctttt cgatctgttg   1680

tttatcgatt ttactcatgc gtatgttcat tacaccattt gttatttgtt taatcaacca   1740

aaagactcat gtttttcaaa tgtctttaat ataatttttc tgattgaatt ttataatatt   1800

tacatgattc tggatccaga atatccttct tcttcttcca ttttgtcctg tattgatttg   1860

tctttgaaaa aggattgttc tttgtatctg tattggtgaa aaaggattgt tatttgttga   1920

taaaaatttg atctttaaac aatgtttggt tttgcataaa ggtagaagac c            1971
```

```
<210> SEQ ID NO 30
<211> LENGTH: 1816
<212> TYPE: DNA
<213> ORGANISM: Artificial Sequence
<220> FEATURE:
<223> OTHER INFORMATION: Synthetic promoter sequence

<400> SEQUENCE: 30

taaatgacat cagatacacg cttgtgaacc atctttaaag tattgatgga ctcttcacta     60

tgaaagctct ctttaaaatt aattttcttt gtacatgtct ctaagcaatg tcaaattaat    120

tagaggtcca aattcaaaaa aatgtcgtat tgaatcattc cattactaaa ttggttcaat    180

gtcagattta aacagcctag agcttctgac gtaagggatg acgcacctga cgtaagggat    240

gacgcacctg acgtaaggga tgacgcacct gacgtaaggg atgacgcact cgagatcccc    300

atctccactg acgtaaggga tgacgcacaa tcccactatc cttcgcaaga cccttcctct    360

atataaggaa gttcatttca tttggagagg acacgctgac aagctagctt ggctgcaggt    420

agatcctagg gataatttag tgagatatga gattctactt tcaacatata ctaatcctaa    480

atctctagca actttttata taagctataa atatcatgaa aatgtatttt aatcgtttca    540

taatttatgc agtcacacta atggaaaaaa ggccaattat tattattttc ttcagactat    600

aaatgaaaac ataaattaaa atgcagatta gtttaaaatt ttaataagta agtaaaatgc    660

ttatagcctt atacaaaatc atatttggaa gtttctaaca ttgttgcaat ttgttatcac    720

aaatcacagt aatatttgta tactaattag taattacaac tatacacaaa tttaaatggg    780

taatcatata tttgtgtcca gtggattgaa caaatatgct cggcccatgc ggaagtaatg    840

ccaattttgg gtgagtaaag cccatgcgaa attttcacat aagaaatgca tgctttttgt    900

tttcaacgac atgagttgca tgctttttat cattgcttat atagttgcaa gtttgcaact    960

ccttgatatt ttttttatgt agacactact accaccaaaa acttttggtc tgcttattct   1020

tgtttactat gtaaaaaaaa taaatgaatt gtttatttac tccgatttga tggagtctgg   1080

tttatgaggt tttatagcct ttacagaaaa ttgatagtta caaaaatatt tttcaaaaat   1140

aaaagggtaa aaccgtcatt tcaagttgtt attgttttgg gggactggat ttgaaatgaa   1200

atatagaacc ggaaaacaag gtgagccgaa gtcgaagcct ttggacccgt tttatattt    1260

actcctccca ttcccttctc cttcaatcct tccttcctcc tcctcccttc ttcttcttcc   1320

cctctttcat tttccagcca ctacaaactt ttctatctct actttttttc ctctcgattt   1380
```

```
caggtacttt ttgagaccct ttgttgtgat tttcgaacac acaccccaat tacgtttgat   1440

ttttgatccc gcatcgattt caattcatcc gtttctgagt ttcttttgga tctgggtgtc   1500

ttgagctaat cttttcgatc tgttgtttat cgattttact catgcgtatg ttcattacac   1560

catttgttat ttgtttaatc aaccaaaaga ctcatgtttt tcaaatgtct ttaatataat   1620

ttttctgatt gaattttata atatttacat gattctggat ccagaatatc cttcttcttc   1680

ttccattttg tcctgtattg atttgtcttt gaaaaaggat tgttctttgt atctgtattg   1740

gtgaaaaagg attgttattt gttgataaaa atttgatctt taaacaatgt ttggttttgc   1800

ataaaggtag aagacc                                                   1816
```

```
<210> SEQ ID NO 31
<211> LENGTH: 1816
<212> TYPE: DNA
<213> ORGANISM: Artificial Sequence
<220> FEATURE:
<223> OTHER INFORMATION: Synthetic promoter sequence

<400> SEQUENCE: 31

taaatgacat cagatacacg cttgtgaacc atctttaaag tattgatgga ctcttcacta     60

tgaaagctct ctttaaaatt aattttcttt gtacatgtct ctaagcaatg tcaaattaat    120

tagaggtcca aattcaaaaa aatgtcgtat tgaatcattc cattactaaa ttggttcaat    180

gtcagattta aacagcctag gatctacctg cagccaagct agcttgtcag cgtgtcctct    240

ccaaatgaaa tgaacttcct tatatagagg aagggtcttg cgaaggatag tgggattgtg    300

cgtcatccct tacgtcagtg gagatgggga tctcgagtgc gtcatccctt acgtcaggtg    360

cgtcatccct tacgtcaggt gcgtcatccc ttacgtcagg tgcgtcatcc cttacgtcag    420

aagctctagg gataatttag tgagatatga gattctactt tcaacatata ctaatcctaa    480

atctctagca actttttata taagctataa atatcatgaa aatgtatttt aatcgtttca    540

taatttatgc agtcacacta atggaaaaaa ggccaattat tattattttc ttcagactat    600

aaatgaaaac ataaattaaa atgcagatta gtttaaaatt ttaataagta agtaaaatgc    660

ttatagcctt atacaaaatc atatttggaa gtttctaaca ttgttgcaat ttgttatcac    720

aaatcacagt aatatttgta tactaattag taattacaac tatacacaaa tttaaatggg    780

taatcatata tttgtgtcca gtggattgaa caaatatgct cggcccatgc ggaagtaatg    840

ccaattttgg gtgagtaaag cccatgcgaa attttcacat aagaaatgca tgctttttgt    900

tttcaacgac atgagttgca tgctttttat cattgcttat atagttgcaa gtttgcaact    960

ccttgatatt ttttttatgt agacactact accaccaaaa acttttggtc tgcttattct   1020

tgtttactat gtaaaaaaaa taaatgaatt gtttatttac tccgatttga tggagtctgg   1080

tttatgaggt tttatagcct ttacagaaaa ttgatagtta caaaaaatatt tttcaaaaat  1140

aaaagggtaa aaccgtcatt tcaagttgtt attgttttgg gggactggat ttgaaatgaa   1200

atatagaacc ggaaaacaag gtgagccgaa gtcgaagcct ttggacccgt ttttatattt   1260

actcctccca ttcccttctc cttcaatcct tccttcctcc tcctcccttc ttcttcttcc   1320

cctctttcat tttccagcca ctacaaactt ttctatctct actttttttc ctctcgattt   1380

caggtacttt ttgagaccct ttgttgtgat tttcgaacac acaccccaat tacgtttgat   1440

ttttgatccc gcatcgattt caattcatcc gtttctgagt ttcttttgga tctgggtgtc   1500

ttgagctaat cttttcgatc tgttgtttat cgattttact catgcgtatg ttcattacac   1560

catttgttat ttgtttaatc aaccaaaaga ctcatgtttt tcaaatgtct ttaatataat   1620
```

ttttctgatt gaattttata atatttacat gattctggat ccagaatatc cttcttcttc 1680
ttccattttg tcctgtattg atttgtcttt gaaaaaggat tgttctttgt atctgtattg 1740
gtgaaaaagg attgttattt gttgataaaa atttgatctt taaacaatgt ttggttttgc 1800
ataaaggtag aagacc 1816

<210> SEQ ID NO 32
<211> LENGTH: 1812
<212> TYPE: DNA
<213> ORGANISM: Artificial Sequence
<220> FEATURE:
<223> OTHER INFORMATION: Synthetic promoter sequence

<400> SEQUENCE: 32
taaatgacat cagatacacg cttgtgaacc atctttaaag tattgatgga ctcttcacta 60
tgaaagctct ctttaaaatt aattttcttt gtacatgtct ctaagcaatg tcaaattaat 120
tagaggtcca aattcaaaaa aatgtcgtat tgaatcattc cattactaaa ttggttcaat 180
gtcagattta aacagcctag ggataattta gtgagatatg agattctact ttcaacatat 240
actaatccta aatctctagc aactttttat ataagctata aatatcatga aaatgtattt 300
taatcgtttc ataatttatg cagtcacact aatggaaaaa aggccaatta ttattatttt 360
cttcagacta taaatgaaaa cataaattaa aatgcagatt agtttaaaat tttaataagt 420
aagtaaaatg cttatagcct tatacaaaat catatttgga agtttctaac attgttgcaa 480
tttgttatca caaatcacag taatatttgt aagcttctga cgtaagggat gacgcacctg 540
acgtaaggga tgacgcacct gacgtaaggg atgacgcacc tgacgtaagg gatgacgcac 600
tcgagatccc catctccact gacgtaaggg atgacgcaca atcccactat ccttcgcaag 660
acccttcctc tatataagga agttcatttc atttggagag gacacgctga caagctagct 720
tggctgcagg tagatctact aattagtaat tacaactata cacaaattta aatgggtaat 780
catatatttg tgtccagtgg attgaacaaa tatgctcggc ccatgcggaa gtaatgccaa 840
ttttgggtga gtaaagccca tgcgaaattt tcacataaga aatgcatgct ttttgttttc 900
aacgacatga gttgcatgct tttatcatt gcttatatag ttgcaagttt gcaactcctt 960
gatatttttt ttatgtagac actactacca ccaaaaactt ttggtctgct tattcttgtt 1020
tactatgtaa aaaaaataaa tgaattgttt atttactccg atttgatgga gtctggttta 1080
tgaggtttta tagcctttac agaaaattga tagttacaaa aatatttttc aaaaataaaa 1140
gggtaaaacc gtcatttcaa gttgttattg ttttgggggga ctggatttga aatgaaatat 1200
agaaccggaa aacaaggtga gccgaagtcg aagcctttgg acccgttttt atatttactc 1260
ctcccattcc cttctccttc aatccttcct tcctcctcct cccttcttct tcttcccctc 1320
tttcattttc cagccactac aaacttttct atctctactt tttttcctct cgatttcagg 1380
tactttttga gacccttttgt tgtgattttc gaacacacac cccaattacg tttgattttt 1440
gatcccgcat cgatttcaat tcatccgttt ctgagtttct tttggatctg ggtgtcttga 1500
gctaatcttt tcgatctgtt gtttatcgat tttactcatg cgtatgttca ttacaccatt 1560
tgttatttgt ttaatcaacc aaaagactca tgtttttcaa atgtctttaa tataattttt 1620
ctgattgaat tttataatat ttacatgatt ctggatccag aatatccttc ttcttcttcc 1680
attttgtcct gtattgattt gtctttgaaa aaggattgtt ctttgtatct gtattggtga 1740
aaaaggattg ttatttgttg ataaaaattt gatctttaaa caatgtttgg ttttgcataa 1800
aggtagaaga cc 1812

<210> SEQ ID NO 33
<211> LENGTH: 1812
<212> TYPE: DNA
<213> ORGANISM: Artificial Sequence
<220> FEATURE:
<223> OTHER INFORMATION: Synthetic promoter sequence

<400> SEQUENCE: 33

```
taaatgacat cagatacacg cttgtgaacc atctttaaag tattgatgga ctcttcacta     60
tgaaagctct ctttaaaatt aattttcttt gtacatgtct ctaagcaatg tcaaattaat    120
tagaggtcca aattcaaaaa aatgtcgtat tgaatcattc cattactaaa ttggttcaat    180
gtcagattta aacagcctag ggataattta gtgagatatg agattctact ttcaacatat    240
actaatccta aatctctagc aactttttat ataagctata aatatcatga aaatgtattt    300
taatcgtttc ataatttatg cagtcacact aatggaaaaa aggccaatta ttattatttt    360
cttcagacta taaatgaaaa cataaattaa aatgcagatt agtttaaaat tttaataagt    420
aagtaaaatg cttatagcct tatacaaaat catatttgga agtttctaac attgttgcaa    480
tttgttatca caaatcacag taatatttgt agatctacct gcagccaagc tagcttgtca    540
gcgtgtcctc tccaaatgaa atgaacttcc ttatatagag gaagggtctt gcgaaggata    600
gtgggattgt gcgtcatccc ttacgtcagt ggagatgggg atctcgagtg cgtcatccct    660
tacgtcaggt gcgtcatccc ttacgtcagg tgcgtcatcc cttacgtcag gtgcgtcatc    720
ccttacgtca gaagcttact aattagtaat tacaactata cacaaattta aatgggtaat    780
catatatttg tgtccagtgg attgaacaaa tatgctcggc ccatgcggaa gtaatgccaa    840
ttttgggtga gtaaagccca tgcgaaattt tcacataaga aatgcatgct tttgttttc     900
aacgacatga gttgcatgct ttttatcatt gcttatatag ttgcaagttt gcaactcctt    960
gatatttttt ttatgtagac actactacca ccaaaaactt ttggtctgct tattcttgtt   1020
tactatgtaa aaaaaataaa tgaattgttt atttactccg atttgatgga gtctggttta   1080
tgaggtttta tagcctttac agaaaattga tagttacaaa aatattttc aaaaataaaa   1140
gggtaaaacc gtcatttcaa gttgttattg ttttggggga ctggatttga aatgaaatat   1200
agaaccggaa aacaaggtga gccgaagtcg aagcctttgg acccgttttt atatttactc   1260
ctcccattcc cttctccttc aatccttcct tcctcctcct cccttcttct tcttcccctc   1320
tttcattttc cagccactac aaacttttct atctctactt tttttcctct cgatttcagg   1380
tactttttga gacccttgt tgtgattttc gaacacacac cccaattacg tttgattttt    1440
gatcccgcat cgatttcaat tcatccgttt ctgagtttct tttggatctg ggtgtcttga   1500
gctaatcttt tcgatctgtt gtttatcgat tttactcatg cgtatgttca ttacaccatt   1560
tgttatttgt ttaatcaacc aaaagactca tgtttttcaa atgtctttaa tataattttt   1620
ctgattgaat tttataatat ttacatgatt ctggatccag aatatccttc ttcttcttcc   1680
attttgtcct gtattgattt gtctttgaaa aaggattgtt ctttgtatct gtattggtga   1740
aaaaggattg ttatttgttg ataaaaattt gatctttaaa caatgtttgg ttttgcataa   1800
aggtagaaga cc                                                       1812
```

<210> SEQ ID NO 34
<211> LENGTH: 1840
<212> TYPE: DNA
<213> ORGANISM: Artificial Sequence
<220> FEATURE:
<223> OTHER INFORMATION: Synthetic promoter sequence

<400> SEQUENCE: 34

```
ggccgcctgc aggaagctgt accccccaag cttaaatgac atcagataca cgcttgtgaa     60
ccatctttaa agtattgatg gactcttcac tatgaaagct ctctttaaaa ttaattttct    120
ttgtacatgt ctctaagcaa tgtcaaatta attagaggtc caaattcaaa aaaatgtcgt    180
attgaatcat tccattacta aattggttca atgtcagatt taaacagcct agggataatt    240
tagtgagata tgagattcta ctttcaacat atactaatcc taaatctcta gcaacttttt    300
atataagcta taaatatcat gaaaatgtat tttaatcgtt tcataattta tgcagtcaca    360
ctaatggaaa aaaggccaat tattattatt ttcttcagac tataaatgaa aacataaatt    420
aaaatgcaga ttagtttaaa attttaataa gtaagtaaaa tgcttatagc cttatacaaa    480
atcatatttg gaagtttcta acattgttgc aatttgttat cacaaatcac agtaatattt    540
gtatactaat tagtaattac aactatacac aaatttaaat gggtaatcat atatttgtgt    600
ccagtggatt gaacaaatat gctcggccca tgcggaagta atgccaattt tgggtgagta    660
aagcccatgc gaaattttca cataagaaaa gcttctgacg taagggatga cgcacctgac    720
gtaagggatg acgcacctga cgtaagggat gacgcacctg acgtaaggga tgacgcactc    780
gagatcccca tctccactga cgtaagggat gacgcacaat cccactatcc ttcgcaagac    840
ccttcctcta tataaggaag ttcatttcat ttggagagga cacgctgaca agctagcttg    900
gctgcaggta gatctgcttt ttgttttcaa cgacatgagt tgcatgcttt ttatcattgc    960
ttatatagtt gcaagtttgc aactccttga tattttttt atgtagacac tactaccacc   1020
aaaaactttt ggtctgctta ttcttgttta ctatgtaaaa aaaataaatg aattgtttat   1080
ttactccgat ttgatggagt ctggtttatg aggttttata gcctttacag aaaattgata   1140
gttacaaaaa tatttttcaa aaataaaagg gtaaaaccgt catttcaagt tgttattgtt   1200
ttgggggact ggatttgaaa tgaaatatag aaccggaaaa caaggtgagc cgaagtcgaa   1260
gcctttggac ccgtttttat atttactcct cccattccct tctccttcaa tccttccttc   1320
ctcctcctcc cttcttcttc ttcccctctt tcattttcca gccactacaa actttttctat  1380
ctctactttt tttcctctcg atttcaggta ctttttgaga ccctttgttg tgattttcga   1440
acacacaccc caattacgtt tgatttttga tcccgcatcg atttcaattc atccgtttct   1500
gagtttcttt tggatctggg tgtcttgagc taatcttttc gatctgttgt ttatcgattt   1560
tactcatgcg tatgttcatt acaccatttg ttatttgttt aatcaaccaa aagactcatg   1620
tttttcaaat gtctttaata taatttttct gattgaattt tataatattt acatgattct   1680
ggatccagaa tatccttctt cttcttccat tttgtcctgt attgatttgt ctttgaaaaa   1740
ggattgttct ttgtatctgt attggtgaaa aaggattgtt atttgttgat aaaaatttga   1800
tctttaaaca atgtttggtt ttgcataaag gtagaagacc                         1840
```

<210> SEQ ID NO 35
<211> LENGTH: 1848
<212> TYPE: DNA
<213> ORGANISM: Artificial Sequence
<220> FEATURE:
<223> OTHER INFORMATION: Synthetic promoter sequence

<400> SEQUENCE: 35

```
ggccgcctgc aggaagctgt accccccaag cttaaatgac atcagataca cgcttgtgaa     60
ccatctttaa agtattgatg gactcttcac tatgaaagct ctctttaaaa ttaattttct    120
ttgtacatgt ctctaagcaa tgtcaaatta attagaggtc caaattcaaa aaaatgtcgt    180
```

-continued

```
attgaatcat tccattacta aattggttca atgtcagatt taaacagcct agggataatt    240
tagtgagata tgagattcta ctttcaacat atactaatcc taaatctcta gcaacttttt    300
atataagcta taaatatcat gaaaatgtat tttaatcgtt tcataattta tgcagtcaca    360
ctaatggaaa aaaggccaat tattattatt ttcttcagac tataaatgaa aacataaatt    420
aaaatgcaga ttagtttaaa attttaataa gtaagtaaaa tgcttatagc cttatacaaa    480
atcatatttg gaagtttcta acattgttgc aatttgttat cacaaatcac agtaatattt    540
gtatactaat tagtaattac aactatacac aaatttaaat gggtaatcat atatttgtgt    600
ccagtggatt gaacaaatat gctcggccca tgcggaagta atgccaattt tgggtgagta    660
aagcccatgc gaaattttca cataagaaat gcatgctttt tgttttcaac gacatgagtt    720
gcatgctttt tatcattgct tatatagttg caagtttgca actccttgat atttttttta    780
tgtagacact actaccacca aaaacttttg gtctgcttat tcttgtttac tatgtaaaaa    840
aaataaatga attgtttatt tactccgatt tgatggagtc tggtttatga ggttttatag    900
cctttacaga aaattgatag ttacaaaaat atttttcaaa aataaaaggg taaaaccgtc    960
atttcaagtt gttattgttt tgggggactg gatttgaaat gaagcttctg acgtaaggga   1020
tgacgcacct gacgtaaggg atgacgcacc tgacgtaagg gatgacgcac ctgacgtaag   1080
ggatgacgca ctcgagatcc ccatctccac tgacgtaagg gatgacgcac aatcccacta   1140
tccttcgcaa gacccttcct ctatataagg aagttcattt catttggaga ggacacgctg   1200
acaagctagc ttggctgcag gtagatcatg aaatatagaa ccggaaaaca aggtgagccg   1260
aagtcgaagc ctttggaccc gtttttatat ttactcctcc cattcccttc tccttcaatc   1320
cttccttcct cctcctccct tcttcttctt cccctctttc attttccagc cactacaaac   1380
ttttctatct ctactttttt tcctctcgat ttcaggtact ttttgagacc ctttgttgtg   1440
attttcgaac acacacccca attacgtttg atttttgatc ccgcatcgat ttcaattcat   1500
ccgtttctga gtttcttttg gatctgggtg tcttgagcta atcttttcga tctgttgttt   1560
atcgatttta ctcatgcgta tgttcattac accatttgtt atttgtttaa tcaaccaaaa   1620
gactcatgtt tttcaaatgt ctttaatata atttttctga ttgaatttta taatatttac   1680
atgattctgg atccagaata tccttcttct tcttccattt tgtcctgtat tgatttgtct   1740
ttgaaaaagg attgttcttt gtatctgtat tggtgaaaaa ggattgttat ttgttgataa   1800
aaatttgatc tttaaacaat gtttggtttt gcataaaggt agaagacc                1848
```

CHIMERIC PROMOTERS COMPRISING A RICE ACTIN 1 PROMOTER AND 35S ENHANCER FOR USE IN PLANTS

This application is a divisional of U.S. application Ser. No. 12/023,350 filed Jan. 31, 2008, now U.S. Pat. No. 7,838,652, that is a continuation of U.S. application Ser. No. 11/038,981, filed Jan. 20, 2005, now U.S. Pat. No. 7,371,848, which claims the benefit of U.S. application 60/537,793 filed Jan. 20, 2004, each of the disclosures of which are incorporated herein by reference in their entirety.

INCORPORATION OF SEQUENCE LISTING

Two copies of the sequence listing (Seq. Listing Copy 1 and Seq. Listing Copy 2) and a computer-readable form of the sequence listing, all on CD-ROMs, each containing the file named pa_01117.rpt, which is 61,440 bytes (measured in MS-DOS) and was created on Jan. 18, 2005 all of which are incorporated herein by reference.

FIELD OF THE INVENTION

The invention relates to the field of plant molecular biology and plant genetic engineering and polynucleotide molecules useful for modulating gene expression in plants.

BACKGROUND

One of the goals of plant genetic engineering is to produce plants with agronomically desirable characteristics or traits. The proper expression of a desirable transgene in a transgenic plant is one way to achieve this goal. Promoters are non-coding polynucleotide molecules which play an integral role in the overall expression of genes in living cells. Isolated promoters that function in plants are useful for modifying plant phenotypes through the methods of genetic engineering.

Many constitutive promoters are available and are useful for providing good overall gene expression. For example, constitutive promoters such as P-FMV, the promoter from the 35S transcript of the Figwort mosaic virus, (U.S. Pat. No. 6,051,753); P-CaMV 35S, the promoter from the 35S RNA transcript of the Cauliflower mosaic virus, (U.S. Pat. No. 5,530,196); P-Rice Actin 1, the promoter from the actin 1 gene of *Oryza sativa*, (U.S. Pat. No. 5,641,876); and P—NOS, the promoter from the nopaline synthase gene of *Agrobacterium tumefaciens* are known to provide some level of gene expression in most or all of the tissues of a plant during most or all of the plant's lifespan. Alternately, many promoters are available with more specific expression patterns such as tissue specificity, temporal specificity, or developmental specificity. These promoters are useful for the targeted expression of a transgene in plants.

Optimal expression of a transgene is useful for producing plants with agronomically desirable characteristics or traits. Such optimal expression often requires a promoter having a specific expression pattern which may not be readily available in known promoters. One example of such a specific expression pattern is a high level of transgene expression in both vegetative and reproductive tissues. The present invention solves this problem by producing novel chimeric promoters containing elements from known promoters. These novel chimeric promoters can then be tested in plants to determine whether the desired expression pattern is indeed achieved.

SUMMARY

In one embodiment the invention provides novel chimeric promoters provided as SEQ ID NO: 9-35 comprising a caulimovirus promoter enhancer fused with a plant actin gene promoter and useful for modulating gene expression in plants. In another embodiment the invention provides constructs comprising the novel chimeric promoter and useful for modulating gene expression in plants. In another embodiment the invention provides a transgenic plant comprising the novel chimeric promoter and the seed of the transgenic plant. In another embodiment the invention provides a method of inhibiting weed growth in a field of transgenic glyphosate tolerant crop plants comprising planting the transgenic plants transformed with an expression cassette comprising the novel chimeric promoter operably linked to a DNA molecule encoding a glyphosate tolerance gene and applying glyphosate to the field at an application rate that inhibits the growth of weeds.

DETAILED DESCRIPTION

Figure 1:
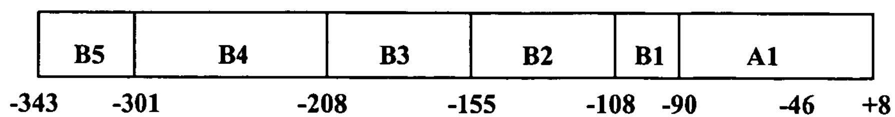
FIG. 1 represents a section of the CaMV 35S promoter with enhancer domains marked. Also diagrammatically represented are five enhancer domains constructed for use in creating chimeric actin promoters.

The following definitions and methods are provided to better define the present invention and to guide those of ordinary skill in the art in the practice of the present invention. Unless otherwise noted, terms are to be understood according to conventional usage by those of ordinary skill in the relevant art.

The invention disclosed herein provides novel combinations of polynucleotide molecules for use in constructing novel chimeric promoters. The design, construction, and use of chimeric or hybrid promoters comprising one or more of the enhancer domains of a caulimovirus 35S promoter and a plant actin gene promoter is one object of this invention. The novel chimeric promoter sequences thereof of SEQ ID NO: 9-35, are capable of transcribing operably linked DNA sequences in multiple tissues and therefore can selectively regulate expression of transgenes in multiple tissues.

As used herein, the term "polynucleotide molecule" refers to the single- or double-stranded DNA or RNA of genomic or synthetic origin, i.e., a polymer of deoxyribonucleotide or ribonucleotide bases, respectively, read from the 5' (upstream) end to the 3' (downstream) end.

As used herein, the term "polynucleotide sequence" refers to the sequence of a polynucleotide molecule. The nomenclature for DNA bases as set forth at 37 CFR §1.822 is used.

As used herein, the term "gene regulatory activity" refers to the ability to affect transcription or translation of an operably linked transcribable polynucleotide molecule. An isolated polynucleotide molecule having gene regulatory activity may provide temporal or spatial expression or modulate levels and rates of expression of the operably linked transcribable polynucleotide molecule. An isolated polynucleotide molecule having gene regulatory activity may comprise a promoter, intron, leader, or 3' transcription termination region.

As used herein, the term "gene expression" refers to the transcription of a DNA molecule into a transcribed RNA molecule. Gene expression may be described as related to temporal, spatial, developmental, or morphological qualities as well as quantitative or qualitative indications.

As used herein, the term "regulatory element" refers to a polynucleotide molecule that may affect the transcription or translation of an operably linked transcribable polynucleotide molecule. Regulatory elements such as promoters, leaders, introns, and transcription termination regions are non-coding polynucleotide molecules having gene regulatory activity which play an integral part in the overall expression of genes in living cells. Isolated regulatory elements that function in plants are therefore useful for modifying plant phenotypes through the methods of genetic engineering.

As used herein, the term "promoter" refers to a polynucleotide molecule that is involved in recognition and binding of RNA polymerase II and other proteins (trans-acting transcription factors) to initiate transcription. A plant promoter is a native or non-native promoter that is functional in plant cells. A promoter can be used as a 5' regulatory element for modulating expression of an operably linked transcribable polynucleotide molecule. Promoters may be defined by their temporal, spatial, or developmental expression pattern.

As used herein, the term "enhancer domain" refers to a cis-acting transcriptional regulatory element, a.k.a. cis-element, which confers an aspect of the overall control of gene expression. An enhancer domain may function to bind transcription factors, trans-acting protein factors that regulate transcription. Some enhancer domains bind more than one transcription factor, and transcription factors may interact with different affinities with more than one enhancer domain. Enhancer domains can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis with known cis-element motifs by conventional DNA sequence comparison methods. The fine structure of an enhancer domain can be further studied by mutagenesis (or substitution) of one or more nucleotides or by other conventional methods. Enhancer domains can be obtained by chemical synthesis or by isolation from promoters that include such elements, and they can be synthesized with additional flanking nucleotides that contain useful restriction enzyme sites to facilitate subsequence manipulation. Thus, the design, construction, and use of enhancer domains according to the methods disclosed herein for modulating the expression of operably linked transcribable polynucleotide molecules are encompassed by the present invention As used herein, the term "chimeric" refers to the product of the fusion of portions of two or more different polynucleotide molecules. As used herein, the term "chimeric promoter" refers to a promoter produced through the manipulation of known promoters or other polynucleotide molecules. Such chimeric promoters may combine enhancer domains that can confer or modulate gene expression from one or more promoters, for example, by fusing a heterologous enhancer domain from a first promoter to a second promoter with its own partial or complete regulatory elements. The novel chimeric promoters of the present invention desirably contain at least one enhancer domain fused to a plant actin promoter. Thus, the design, construction, and use of chimeric promoters according to the methods disclosed herein for modulating the expression of operably linked transcribable polynucleotide molecules are encompassed by the present invention.

As used herein, the term "percent sequence identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG® Wisconsin Package® (Accelrys Inc., Burlington, Mass.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence.

As used herein, the term "substantial percent sequence identity" refers to a percent sequence identity of at least about 80% sequence identity, at least about 90% sequence identity, or even greater sequence identity, such as about 98% or about 99% sequence identity. Thus, one embodiment of the invention is a polynucleotide molecule that has at least about 80% sequence identity, at least about 90% sequence identity, or even greater sequence identity, such as about 98% or about 99% sequence identity with a polynucleotide sequence described herein. Polynucleotide molecules that are capable of regulating transcription of operably linked transcribable polynucleotide molecules and have a substantial percent sequence identity to the polynucleotide sequences of the promoters provided herein are encompassed within the scope of this invention.

Promoter Isolation and Modification Methods

Any number of methods well known to those skilled in the art can be used to isolate fragments of a promoter disclosed herein. For example, PCR (polymerase chain reaction) technology can be used to amplify flanking regions from a genomic library of a plant using publicly available sequence information. A number of methods are known to those of skill in the art to amplify unknown polynucleotide molecules adjacent to a core region of known polynucleotide sequence. Methods include but are not limited to inverse PCR (IPCR), vectorette PCR, Y-shaped PCR, and genome walking approaches. Polynucleotide fragments can also be obtained by other techniques such as by directly synthesizing the fragment by chemical means, as is commonly practiced by using an automated oligonucleotide synthesizer. For the present invention, the polynucleotide molecules were isolated by designing PCR primers based on available sequence information.

Novel chimeric promoters can be designed or engineered by a number of methods. For example, a chimeric promoter may be produced by fusing an enhancer domain from a first promoter to a second promoter. The resultant chimeric promoter may have novel expression properties relative to the first or second promoters. Novel chimeric promoters can be constructed such that the enhancer domain from a first promoter is fused at the 5' end, at the 3' end, or at any position internal to the second promoter. The location of the enhancer domain fusion relative to the second promoter may cause the resultant chimeric promoter to have novel expression properties relative to a fusion made at a different location.

Those of skill in the art are familiar with the standard resource materials that describe specific conditions and procedures for the construction, manipulation, and isolation of macromolecules (e.g., polynucleotide molecules, plasmids, etc.), as well as the generation of recombinant organisms and the screening and isolation of polynucleotide molecules.

Constructs

As used herein, the term "construct" refers to any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more transcribable polynucleotide molecule has been operably linked.

As used herein, the term "operably linked" refers to a first polynucleotide molecule, such as a promoter, connected with a second transcribable polynucleotide molecule, such as a gene of interest, where the polynucleotide molecules are so arranged that the first polynucleotide molecule affects the function of the second polynucleotide molecule. The two polynucleotide molecules may be part of a single contiguous polynucleotide molecule and may be adjacent. For example, a promoter is operably linked to a gene of interest if the promoter regulates or mediates transcription of the gene of interest in a cell.

As used herein, the term "transcribable polynucleotide molecule" refers to any polynucleotide molecule capable of being transcribed into a RNA molecule. Methods are known for introducing constructs into a cell in such a manner that the transcribable polynucleotide molecule is transcribed into a functional mRNA molecule that is translated and therefore expressed as a protein product. Constructs may also be constructed to be capable of expressing antisense RNA molecules, in order to inhibit translation of a specific RNA molecule of interest. For the practice of the present invention, conventional compositions and methods for preparing and using constructs and host cells are well known to one skilled in the art, see for example, *Molecular Cloning: A Laboratory Manual,* 3$^{rd}$ *edition Volumes* 1, 2, *and* 3 (2000). J. F. Sambrook, D. W. Russell, and N. Irwin, Cold Spring Harbor Laboratory Press.

Constructs of the present invention would typically contain a promoter operably linked to a transcribable polynucleotide molecule operably linked to a 3' transcription termination polynucleotide molecule. In addition, constructs may include but are not limited to additional regulatory polynucleotide molecules from the 3'-untranslated region (3' UTR) of plant genes (e.g., a 3' UTR to increase mRNA stability of the mRNA, such as the PI-II termination region of potato or the octopine or nopaline synthase 3' termination regions). Constructs may include but are not limited to the 5' untranslated regions (5' UTR) of an mRNA polynucleotide molecule which can play an important role in translation initiation and can also be a genetic component in a plant expression construct. For example, non-translated 5' leader polynucleotide molecules derived from heat shock protein genes have been demonstrated to enhance gene expression in plants (see for example, U.S. Pat. Nos. 5,659,122 and 5,362,865, all of which are incorporated herein by reference). These additional upstream and downstream regulatory polynucleotide molecules may be derived from a source that is native or heterologous with respect to the other elements present on the construct.

Thus, one embodiment of the invention is a promoter such as provided in SEQ ID NO: 9-35, operably linked to a transcribable polynucleotide molecule so as to direct transcription of said transcribable polynucleotide molecule at a desired level or in a desired tissue or developmental pattern upon introduction of said construct into a plant cell. In one embodiment, the transcribable polynucleotide molecule comprises a protein-coding region of a gene, and the promoter provides for transcription of a functional mRNA molecule that is translated and expressed as a protein product. In another embodiment, the transcribable polynucleotide molecule comprises an antisense region of a gene, and the regulatory element affects the transcription of an antisense RNA molecule or other similar inhibitory RNA in order to inhibit expression of a specific RNA molecule of interest in a target host cell.

Exemplary transcribable polynucleotide molecules for incorporation into constructs of the present invention include, for example, polynucleotide molecules or genes from a species other than the target species or genes that originate with or are present in the same species, but are incorporated into recipient cells by genetic engineering methods rather than classical reproduction or breeding techniques. The type of polynucleotide molecule can include but is not limited to a polynucleotide molecule that is already present in the plant cell, a polynucleotide molecule from another plant, a polynucleotide molecule from a different organism, or a polynucleotide molecule generated externally, such as a polynucleotide molecule containing an antisense message of a gene, or a polynucleotide molecule encoding an artificial, synthetic, or otherwise modified version of a transgene.

The regulatory elements of the present invention can be incorporated into a construct using marker genes as described and tested in transient or stable plant analyses to provide an indication of the regulatory element's gene expression pattern in stable transgenic plants. As used herein the term "marker gene" refers to any transcribable polynucleotide molecule whose expression can be screened for or scored in some way. Marker genes for use in the practice of the present invention include, but are not limited to transcribable polynucleotide molecules encoding B-glucuronidase (GUS described in U.S. Pat. No. 5,599,670, which is incorporated herein by reference) and green fluorescent protein (GFP described in U.S. Pat. Nos. 5,491,084 and 6,146,826, both of which are incorporated herein by reference), proteins that confer antibiotic resistance, or proteins that confer herbicide tolerance. Useful antibiotic resistance markers, including those encoding proteins conferring resistance to kanamycin (nptII), hygromycin B (aph IV), streptomycin or spectinomycin (aad, spec/strep) and gentamycin (aac3 and aacC4) are known in the art. Herbicides for which transgenic plant tolerance has been demonstrated and the method of the present invention can be applied, include but are not limited to: glyphosate, glufosinate, sulfonylureas, imidazolinones, bromoxynil, delapon, cyclohezanedione, protoporphyrionogen oxidase inhibitors, and isoxasflutole herbicides. Polynucleotide molecules encoding proteins involved in herbicide tolerance are known in the art, and include, but are not limited to a polynucleotide molecule encoding 5-enolpyruvylshikimate-3-phosphate synthase (EPSPS described in U.S. Pat.

Nos. 5,627,061, 6,040,497 and in U.S. Pat. No. 5,094,945 for glyphosate tolerance, all of which are incorporated herein by reference); polynucleotides encoding a glyphosate oxidoreductase and a glyphosate-N-acetyl transferase (GOX described in U.S. Pat. No. 5,463,175 and GAT described in U.S. Patent publication 20030083480, both of which are incorporated herein by reference); a polynucleotide molecule encoding bromoxynil nitrilase (Bxn described in U.S. Pat. No. 4,810,648 for Bromoxynil tolerance, which is incorporated herein by reference); a polynucleotide molecule encoding phytoene desaturase (crtI) described in Misawa et al, (1993) *Plant J.* 4:833-840 and Misawa et al, (1994) *Plant J.* 6:481-489 for norflurazon tolerance; a polynucleotide molecule encoding acetohydroxyacid synthase (AHAS, aka ALS) described in Sathasiivan et al. (1990) *Nucl. Acids Res.* 18:2188-2193 for tolerance to sulfonylurea herbicides; a polynucleotide molecule encoding a dicamba-degrading oxygenase enzyme (described in U.S. Patent Publications US20030135879 and US20030115626, for dicamba tolerance, all of which are incorporated herein by reference); and the bar gene described in DeBlock, et al. (1987) *EMBO J.* 6:2513-2519 for glufosinate and bialaphos tolerance. The regulatory elements of the present invention can express transcribable polynucleotide molecules that encode for phosphinothricin acetyltransferase, glyphosate resistant EPSPS, aminoglycoside phosphotransferase, hydroxyphenyl pyruvate dehydrogenase, hygromycin phosphotransferase, neomycin phosphotransferase, dalapon dehalogenase, bromoxynil resistant nitrilase, anthranilate synthase, glyphosate oxidoreductase and glyphosate-N-acetyl transferase.

Thus, in one embodiment of the invention, a polynucleotide molecule of the present invention as shown in SEQ ID NO: 9-35 is incorporated into a DNA construct such that a polynucleotide molecule of the present invention is operably linked to a transcribable polynucleotide molecule that provides for a selectable, screenable, or scorable marker. The constructs containing the regulatory elements operably linked to a marker gene may be delivered to the tissues and the tissues analyzed by the appropriate mechanism, depending on the marker. The quantitative or qualitative analyses are used as a tool to evaluate the potential expression profile of a regulatory element when operatively linked to a gene of agronomic interest in stable plants. Any marker gene can be used in a transient assay. Methods of testing for marker gene expression in transient assays are known to those of skill in the art. Transient expression of marker genes has been reported using a variety of plants, tissues, and DNA delivery systems. For example, types of transient analyses can include but are not limited to direct gene delivery via electroporation or particle bombardment of tissues in any transient plant assay using any plant species of interest. Such transient systems would include but are not limited to electroporation of protoplasts from a variety of tissue sources or particle bombardment of specific tissues of interest. The present invention encompasses the use of any transient expression system to evaluate regulatory elements operably linked to any transcribable polynucleotide molecule, including but not limited to marker genes or genes of agronomic interest. Examples of plant tissues envisioned to test in transients via an appropriate delivery system would include but are not limited to leaf base tissues, callus, cotyledons, roots, endosperm, embryos, floral tissue, pollen, and epidermal tissue.

In one embodiment of the invention, a polynucleotide molecule as shown in SEQ ID NO: 9-35 is incorporated into a construct such that a polynucleotide molecule of the present invention is operably linked to a transcribable polynucleotide molecule that is a gene of agronomic interest. As used herein, the term "gene of agronomic interest" refers to a transcribable polynucleotide molecule that includes but is not limited to a gene that provides a desirable characteristic associated with plant morphology, physiology, growth and development, yield, nutritional enhancement, disease or pest resistance, or environmental or chemical tolerance. The expression of a gene of agronomic interest is desirable in order to confer an agronomically important trait. A gene of agronomic interest that provides a beneficial agronomic trait to crop plants may be, for example, including, but not limited to genetic elements comprising herbicide resistance (U.S. Pat. Nos. 6,803,501; 6,448,476; 6,248,876; 6,225,114; 6,107,549; 5,866,775; 5,804,425; 5,633,435; 5,463,175; and U.S. Patent Publications US20030135879 and US20030115626), increased yield (U.S. Pat. RE38,446; U.S. Pat. Nos. 6,716,474; 6,663,906; 6,476,295; 6,441,277; 6,423,828; 6,399,330; 6,372,211; 6,235,971; 6,222,098; 5,716,837), insect control (U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658, 5,880,275; 5,763,245; 5,763,241), fungal disease resistance (U.S. Pat. Nos. 6,653,280; 6,573,361; 6,506,962; 6,316,407; 6,215,048; 5,516,671; 5,773,696; 6,121,436; 6,316,407; 6,506,962), virus resistance (U.S. Pat. Nos. 6,617,496; 6,608,241; 6,015,940; 6,013,864; 5,850,023; 5,304,730), nematode resistance (U.S. Pat. No. 6,228,992), bacterial disease resistance (U.S. Pat. No. 5,516,671), plant growth and development (U.S. Pat. Nos. 6,723,897; 6,518,488), starch production (U.S. Pat. Nos. 6,538,181; 6,538,179; 6,538,178; 5,750,876; 6,476,295), modified oils production (U.S. Pat. Nos. 6,444,876; 6,426,447; 6,380,462), high oil production (U.S. Pat. Nos. 6,495,739; 5,608,149; 6,483,008; 6,476,295), modified fatty acid content (U.S. Pat. Nos. 6,828,475; 6,822,141; 6,770,465; 6,706,950; 6,660,849; 6,596,538; 6,589,767; 6,537,750; 6,489,461; 6,459,018), high protein production (U.S. Pat. No. 6,380,466), fruit ripening (U.S. Pat. No. 5,512,466), enhanced animal and human nutrition (U.S. Pat. Nos. 6,723,837; 6,653,530; 6,5412,59; 5,985,605; 6,171,640), biopolymers (U.S. Pat. RE37,543; U.S. Pat. Nos. 6,228,623; 5,958,745 and U.S. Patent Publication No. US20030028917), environmental stress resistance (U.S. Pat. No. 6,072,103), pharmaceutical peptides and secretable peptides (U.S. Pat. Nos. 6,812,379; 6,774,283; 6,140,075; 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), fiber production (U.S. Pat. Nos. 6,576,818; 6,271,443; 5,981,834; 5,869,720) and biofuel production (U.S. Pat. No. 5,998,700); the genetic elements, methods, and transgenes described in the patents listed above are incorporated herein by reference.

Alternatively, a transcribable polynucleotide molecule can effect the above mentioned plant characteristic or phenotypes by encoding a RNA molecule that causes the targeted inhibition of expression of an endogenous gene, for example via antisense, inhibitory RNA (RNAi), or cosuppression-mediated mechanisms. The RNA could also be a catalytic RNA molecule (i.e., a ribozyme) engineered to cleave a desired endogenous mRNA product. Thus, any transcribable polynucleotide molecule that encodes a transcribed RNA molecule that affects a phenotype or morphology change of interest may be useful for the practice of the present invention.

The constructs of the present invention are generally double Ti plasmid border DNA constructs that have the right border (RB or AGRtu.RB) and left border (LB or AGRtu.LB) regions of the Ti plasmid isolated from *Agrobacterium tumefaciens* comprising a T-DNA, which along with transfer molecules provided by the *Agrobacterium* cells, permit the integration of the T-DNA into the genome of a plant cell. The constructs may also contain the plasmid backbone DNA segments that provide replication function and antibiotic selection in bacterial cells, for example, an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *Agrobacterium tumefaciens* ABI, C58, or LBA4404, however, other strains known to those skilled in the art of plant transformation can function in the present invention.

Transformed Plants and Plant Cells

As used herein, the term "transformed" refers to a cell, tissue, organ, or organism into which has been introduced a foreign polynucleotide molecule, such as a construct. The introduced polynucleotide molecule may be integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic plant as a parent in a cross and exhibiting an altered phenotype resulting from the presence of a foreign polynucleotide molecule. A plant transformation construct containing a promoter of the present invention may be introduced into plants by any plant transformation method. Methods and materials for transforming plants by introducing a plant expression construct into a plant genome in the practice of this invention can include any of the well-known and demonstrated methods including electroporation (as illustrated in U.S. Pat. No. 5,384,253; microprojectile bombardment as illustrated in U.S. Pat. Nos. 5,015,580; 5,550,318; 5,538,880; 6,160,208; 6,399,861; and 6,403,865; *Agrobacterium*-mediated transformation as illustrated in U.S. Pat. Nos. 5,824,877; 5,591,616; 5,981,840; and 6,384,301; and protoplast transformation as illustrated in U.S. Pat. No. 5,508,184, all of which are incorporated herein by reference.

Methods for specifically transforming dicots are well known to those skilled in the art. Transformation and plant regeneration using these methods have been described for a number of crops including, but not limited to, cotton (*Gossypium hirsutum*), soybean (*Glycine max*), peanut (*Arachis hypogaea*), and members of the genus *Brassica*.

Methods for transforming monocots are well known to those skilled in the art. Transformation and plant regeneration using these methods have been described for a number of crops including, but not limited to, barley (*Hordeum vulgarae*); maize (*Zea mays*); oats (*Avena sativa*); orchard grass (*Dactylis glomerata*); rice (*Oryza sativa*, including indica and japonica varieties); sorghum (*Sorghum bicolor*); sugar cane (*Saccharum* sp); tall fescue (*Festuca arundinacea*); turfgrass species (e.g. species: *Agrostis stolonifera, Poa pratensis, Stenotaphrum secundatum*); wheat (*Triticum aestivum*), and alfalfa (*Medicago sativa*). It is apparent to those of skill in the art that a number of transformation methodologies can be used and modified for production of stable transgenic plants from any number of target crops of interest.

The transformed plants are analyzed for the presence of the genes of interest and the expression level and/or profile conferred by the promoters of the present invention. Those of skill in the art are aware of the numerous methods available for the analysis of transformed plants. For example, methods for plant analysis include, but are not limited to Southern blots or northern blots, PCR-based approaches, biochemical analyses, phenotypic screening methods, field evaluations, and immunodiagnostic assays.

The seeds of this invention can be harvested from fertile transgenic plants and be used to grow progeny generations of transformed plants of this invention including hybrid plant lines comprising the construct of this invention and expressing a gene of agronomic interest.

The present invention also provides for parts of the plants of the present invention. Plant parts, without limitation, include seed, endosperm, ovule and pollen. In a particularly preferred embodiment of the present invention, the plant part is a seed.

Still yet another aspect of the invention is a method of inhibiting weed growth in a field of transgenic crop plants comprising first planting the transgenic plants transformed with an expression cassette comprising a polynucleotide sequence selected from the group consisting of SEQ ID NO: 9-35 operably linked to a transcribable polynucleotide molecule encoding a glyphosate tolerance gene and then applying glyphosate to the field at an application rate that inhibits the growth of weeds, wherein the growth and yield of the transgenic crop plant is not substantially affected by the glyphosate application. The glyphosate application rate is the effective rate necessary to control weeds in a particular glyphosate tolerant crop; these rates may range from 8 ounces/acre to 256 ounces/acre, preferably 16 ounces/acre to 128 ounces/acre, and more preferably 32 ounces/acre to 96 ounces/acre. The glyphosate is applied at least once during the growth of the glyphosate tolerant crop and may be applied 2, 3, or 4 times during the growth of the crop or more as necessary to control weeds in the field.

The following examples are included to demonstrate preferred embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1

Construction of Chimeric Promoters

Novel chimeric promoters are constructed by fusing at least one enhancer domain from a Caulimovirus promoter with a plant actin gene promoter. A brief description of the sequences referred to herein is provided in Table 1 below.

TABLE 1

Brief Listing of the SEQ ID NO

| SEQ ID NO | Sequence Name | Brief Description |
|---|---|---|
| 1 | P-CaMV.35S | 35S promoter sequence from the Cauliflower mosaic virus |
| 2 | 4xB3 | P-CaMV.35S Enhancer Domain -- four tandem copies of the B3 domain (−208 to −155) as described in U.S. Pat. No. 5,097,025 |
| 3 | 4xAS-1 | P-CaMV.35S Enhancer Domain -- four tandem copies of the “activation sequence” (−83 to −62) as described in U.S. Pat. No. 5,097,025 |
| 4 | 2xB1-B2 | P-CaMV.35S Enhancer Domain -- two tandem copies of the B1-B2 domain (−148 to −90) as described in U.S. Pat. No. 5,097,025 |
| 5 | 2xA1-B3 | P-CaMV.35S Enhancer Domain -- two tandem copies of the A1-B3 domain (−208 to −46) as described in U.S. Pat. No. 5,097,025 |
| 6 | 2xB1-B5 | P-CaMV.35S Enhancer Domain -- two tandem copies of the B1-B5 domain (−343 to −90) as described in U.S. Pat. No. 5,097,025 |
| 7 | P-Os.Act1 | Rice actin 1 promoter |
| 8 | P-At.Act1 | *Arabidopsis* Actin 1 promoter |
| 9 | P-4xB3/P-Os.Act1-1 | Chimeric promoter -- 4xB3 fused to the rice Act1 promoter at the −848 nt position |
| 10 | P-4xB3/P-Os.Act1-2 | Chimeric promoter -- 4xB3 fused to the rice Act1 promoter at the −462 nt position |
| 11 | P-4xB3/P-Os.Act1-3 | Chimeric promoter -- 4xB3 fused to the rice Act1 promoter at the −80 nt position |
| 12 | P-4xAS-1/P-Os.Act1-1 | Chimeric promoter -- 4xAS-1 fused to the rice Act1 promoter at the −848 nt position |
| 13 | P-4xAS-1/P-Os.Act1-2 | Chimeric promoter -- 4xAS-1 fused to the rice Act1 promoter at the −462 nt position |
| 14 | P-4xAS-1/P-Os.Act1-3 | Chimeric promoter -- 4xAS-1 fused to the rice Act1 promoter at the −80 nt position |
| 15 | P-2xB1-B2/P-Os.Act1-1 | Chimeric promoter -- 2xB1-B2 fused to the rice Act1 promoter at the −848 nt position |
| 16 | P-2xB1-B2/P-Os.Act1-2 | Chimeric promoter -- 2xB1-B2 fused to the rice Act1 promoter at the −462 nt position |
| 17 | P-2xB1-B2/P-Os.Act1-3 | Chimeric promoter -- 2xB1-B2 fused to the rice Act1 promoter at the −80 nt position |
| 18 | P-2xA1-B3/P-Os.Act1-1 | Chimeric promoter -- 2xA1-B3 fused to the rice Act1 promoter at the −848 nt position |
| 19 | P-2xA1-B3/P-Os.Act1-2 | Chimeric promoter -- 2xA1-B3 fused to the rice Act1 promoter at the −462 nt position |
| 20 | P-2xA1-B3/P-Os.Act1-3 | Chimeric promoter -- 2xA1-B3 fused to the rice Act1 promoter at the −80 nt position |
| 21 | P-2xB1-B5/P-Os.Act1-1 | Chimeric promoter -- 2xB1-B5 fused to the rice Act1 promoter at the −848 nt position |
| 22 | P-2xB1-B5/P-Os.Act1-2 | Chimeric promoter -- 2xB1-B5 fused to the rice Act1 promoter at the −462 nt position |
| 23 | P-2xB1-B5/P-Os.Act1-3 | Chimeric promoter -- 2xB1-B5 fused to the rice Act1 promoter at the −80 nt position |
| 24 | P-2xA1-B3/At.Act1/ArvII | Chimeric promoter -- 2xA1-B3 fused to the *Arabidopsis* Act1 promoter at the ArvII position |
| 25 | P-2xA1-B3/At.Act1/BstZI | Chimeric promoter -- 2xA1-B3 fused to the *Arabidopsis* Act1 promoter at the BstZI position |
| 26 | P-2xA1-B3/At.Act1/BstZI-R | Chimeric promoter -- 2xA1-B3 fused to the *Arabidopsis* Act1 promoter at the BstZI position in reverse orientation |
| 27 | P-2xA1-B3/At.Act1/NsiI | Chimeric promoter -- 2xA1-B3 fused to the *Arabidopsis* Act1 promoter at the NsiI position |
| 28 | P-2xA1-B3/At.Act1/NsiI-R | Chimeric promoter -- 2xA1-B3 fused to the *Arabidopsis* Act1 promoter at the NsiI position in reverse orientation |
| 29 | P-2xA1-B3/At.Act1/BsmFI | Chimeric promoter -- 2xA1-B3 fused to the *Arabidopsis* Act1 promoter at the BsmFI position |
| 30 | P-4xAS-1/At.Act1/ArvII | Chimeric promoter -- 4xAS-1 fused to the *Arabidopsis* Act1 promoter at the ArvII position |
| 31 | P-4xAS-1/At.Act1/ArvII-R | Chimeric promoter -- 4xAS-1 fused to the *Arabidopsis* Act1 promoter at the ArvII position in reverse orientation |
| 32 | P-4xAS-1/At.Act1/BstZI | Chimeric promoter -- 4xAS-1 fused to the *Arabidopsis* Act1 promoter at the BstZi position |
| 33 | P-4xAS-1/At.Act1/BstZI-R | Chimeric promoter -- 4xAS-1 fused to the *Arabidopsis* Act1 promoter at the BstZI position in reverse orientation |
| 34 | P-4xAS-1/At.Act1/NsiI | Chimeric promoter -- 4xAS-1 fused to the *Arabidopsis* Act1 promoter at the NsiI position |
| 35 | P-4xAS-1/At.Act1/BsmFI | Chimeric promoter -- 4xAS-1 fused to the *Arabidopsis* Act1 promoter at the BsmFI position |

The Caulimovirus promoter can be any promoter from a virus in the Caulimovirus family, including but not limited to promoters from Cauliflower mosaic virus (CaMV) such as the promoter from the 35S RNA transcript of the Cauliflower mosaic virus (P-CaMV.35S) (SEQ ID NO: 1) (U.S. Pat. No. 5,530,196) and promoters from Figwort mosaic virus (FMV) such as the promoter from the 35S transcript of the Figwort mosaic virus, (U.S. Pat. No. 6,051,753), all of which are incorporated herein by reference. Promoter enhancer domains constructed as multimers of enhancer domains from the P-CaMV.35S promoter include but are not limited to the 4xB3 domain (SEQ ID NO: 2), 4xAS-1 (SEQ ID NO: 3), 2xB1-B2 domain (SEQ ID NO: 4), 2xA1-B3 domain (SEQ ID NO: 5), and 2xB1-B5 domain (SEQ ID NO: 6). See FIG. 1. The monomers comprising the multimers listed above as well as other enhancer domains from P-CaMV.35S are described in U.S. Pat. No. 5,097,025, incorporated herein by reference.

The plant actin gene promoter can be any promoter from a plant actin gene, including but not limited to actin promoters from *Oryza sativa* such as the rice actin 1 promoter (P-Os.Act1) (SEQ ID NO: 7) (U.S. Pat. No. 5,641,876), actin promoters from *Arabidopsis thaliana* such as the *Arabidopsis* Actin 1 promoter (P-At.Act1) (SEQ ID NO: 8), and actin promoters from *Zea mays* such as the Actin-2 promoter (U.S. Pat. No. 6,670,467), all of which are incorporated herein by reference.

The fusion of at least one enhancer domain with a plant actin gene promoter may be to any region of the plant actin gene promoter including but not limited to the 5' end of the plant actin gene promoter, the 3' end of the plant actin gene promoter, or any region internal to the plant actin gene promoter. The enhancer domain may be in either the reverse or the forward orientation.

Figure 2:
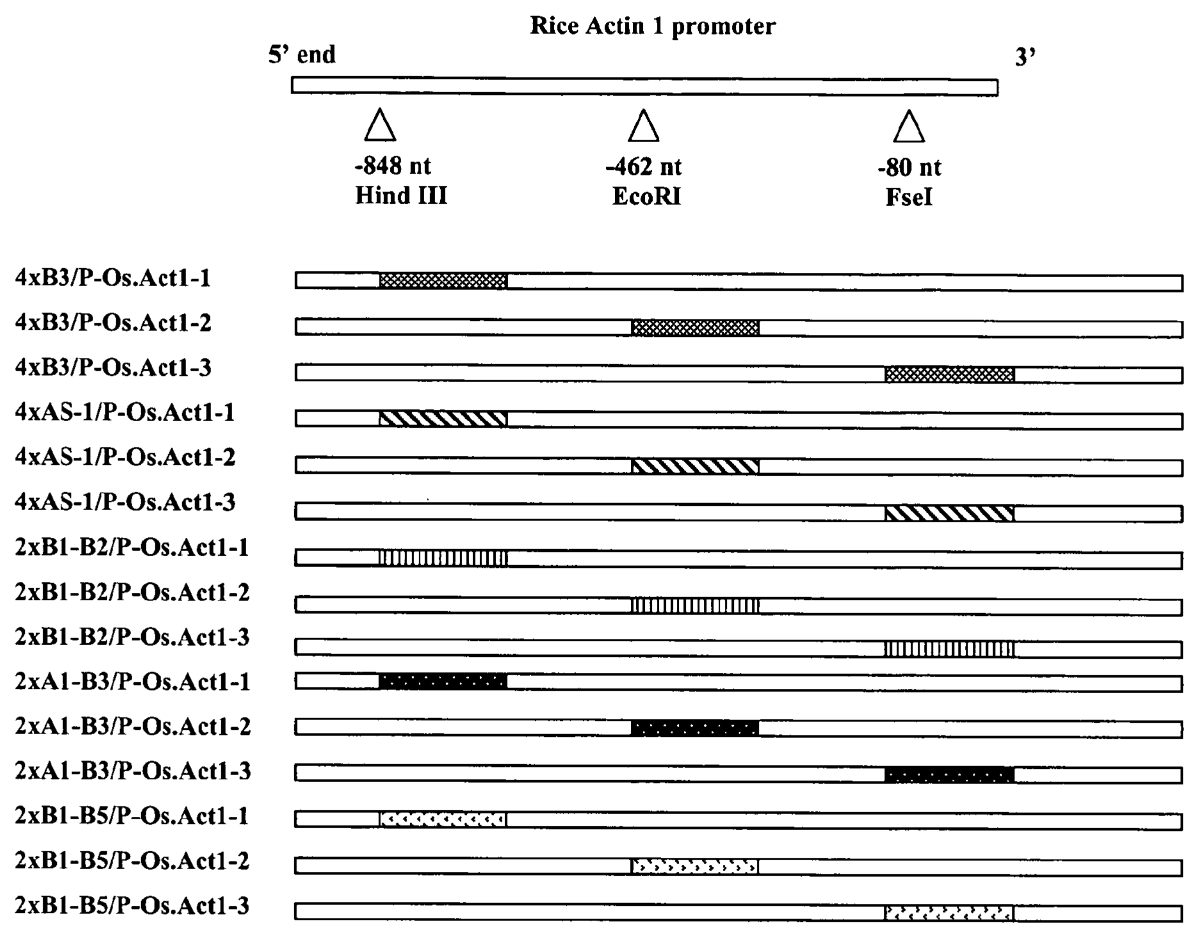
FIG. 2 represents the native rice actin 1 promoter and novel chimeric promoters made by fusing the rice actin 1 promoter and selected CaMV 35S promoter enhancer domains.

Enhancer domains derived from P-CaMV.35S were inserted in three locations in the rice actin 1 (relative to rice Actin1 transcription initiation site): −848 nt (HindIII site), −462 nt (EcoRI site), and −80 nt (FseI site). See FIG. 2. Construction of these chimeric promoters is described in detail below.

The P-4xB3/P-Os.Act1 chimeric promoters were created by fusing the four tandem copies CaMV 35S B3 enhancer sequence to the rice Act1 promoter (P-Os.Act1). Chimeras were made by fusing the enhancer region at the −848 nt position of P-Os.Act1 (SEQ ID NO: 9), at the −462 nt position of P-Os.Act1 (SEQ ID NO: 10) and at the −80 nt position of P-Os.Act1 (SEQ ID NO: 11).

The P-4xAS-1/P-Os.Act1 chimeric promoter was created by fusing four tandem copies of the CaMV 35S AS-1 enhancer sequence to the rice Act1 promoter (P-Os.Act1). Chimeras were made by fusing the enhancer region at the −848 nt position of P-Os.Act1 (SEQ ID NO: 12), at the −462 nt position of P-Os.Act1 (SEQ ID NO: 13) and at the −80 nt position of P-Os.Act1 (SEQ ID NO: 14).

The P-2xB1-B2/P-Os.Act1 chimeric promoter was created by fusing two tandem copies of the CaMV 35S B1-B2 enhancer sequence to the rice Act1 promoter (P-Os.Act1). Chimeras were made by fusing the enhancer region at the −848 nt position of P-Os.Act1 (SEQ ID NO: 15), at the −462 nt position of P-Os.Act1 (SEQ ID NO: 16) and at the −80 nt position of P-Os.Act1 (SEQ ID NO: 17).

The P-2xA1-B3/P-Os.Act1 chimeric promoters were created by fusing two tandem copies of the CaMV 35S A1-B3 enhancer sequence to the rice Act1 promoter (P-Os.Act1). Chimeras were made by fusing the enhancer region at the −848 nt position of P-Os.Act1 (SEQ ID NO: 18), at the −462 nt position of P-Os.Act1 (SEQ ID NO: 19), and at the −80 nt position of P-Os.Act1 (SEQ ID NO: 20).

The P-2xB1-B5/P-Os.Act1 chimeric promoter was created by fusing two tandem copies of the CaMV 35S B1-B5 enhancer sequence to the rice Act1 promoter (P-Os.Act1). Chimeras were made by fusing the enhancer region at the −848 nt position of P-Os.Act1 (SEQ ID NO: 21), at the −462 nt position of P-Os.Act1 (SEQ ID NO: 22) and at the −80 nt position of P-Os.Act1 (SEQ ID NO: 23).

Enhancer domains derived from P-CaMV.35S were inserted in four locations in the *Arabidopsis* actin 1 promoter (P-At.Act1) (with the P-At.Act1 transcription initiation site designated as +1). Four unique restriction sites in P-At.Act1 were used as insertion sites: AvrII, BstZI, NsiI, BsmFI. Construction of these chimeric promoters is described in detail below.

Figure 3:
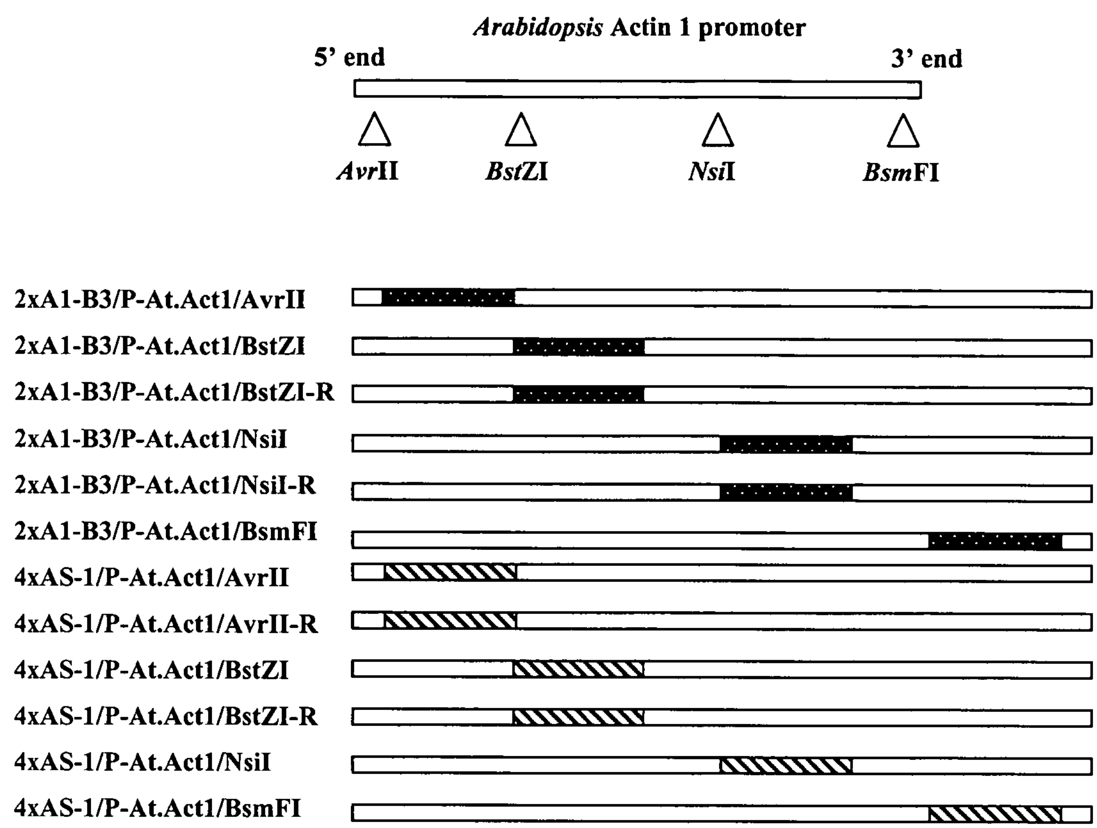
FIG. 3 represents the native *Arabidopsis* actin 1 promoter and novel chimeric promoters made by fusing the *Arabidopsis* actin 1 promoter and selected CaMV 35S promoter enhancer domains.

The 2xA1B3 and 4xAS-1 fragments were isolated by restriction enzyme digest. Fragments ends were then made blunt by treatment with T4 DNA polymerase. Vectors containing the P-At.Act1 promoter were cut with one of the four unique enzymes and then the fragment ends were made blunt. Each of the two enhancer domains was fused into each of the four blunted restriction enzyme sites. Chimeric promoters were selected with inserts in both the reverse and forward orientations. See FIG. 3.

Selected chimeric promoters were subcloned into a binary vector to operably link the chimeric promoter with a reporter gene such as the GUS reporter gene (β-glucuronidase gene) or the CP4 gene (for glyphosate tolerance). These vectors were used for plant transformation and subsequent promoter characterization. Transgene expression levels of the chimeric promoters were compared with the transgene expression levels of control constructs.

Example 2

Promoter Characterization in Transient Systems

Selected chimeric promoters were used for transient transformation for reporter expression analysis. Transient systems used included tobacco protoplasts, corn protoplasts, wheat ovary, wheat anther, and barley microspores. Cells were harvested and protein extracted for GUS activity analysis. Methods for measuring GUS activity are well known to those skilled in the art, see for instance *Using the Gus Gene as a Reporter of Gene Expression* (1992) edited by Sean R. Gallagher, Academic Press, Inc., San Diego.

Monocot Analysis

Constructs containing chimeric P-Os.Act1 promoters were used to transform corn protoplasts and assay for GUS/LUX activity relative to the P-Os.Act1 promoter and the P-CaMV.e35S promoter. Data are provided in Table 2.

TABLE 2

Transient Analysis in Corn Protoplasts

| Chimeric Promoter | SEQ ID NO | Construct | Relative activity |
|---|---|---|---|
| P-Os.Act1 | 7 | pMON25455 | 1.0 |
| P-2xB1-B5/P-Os.Act1-1 | 21 | pMON38303 | 1.6 |
| P-2xB1-B5/P-Os.Act1-2 | 22 | pMON38304 | 1.1 |

TABLE 2-continued

| Transient Analysis in Corn Protoplasts | | | |
|---|---|---|---|
| Chimeric Promoter | SEQ ID NO | Construct | Relative activity |
| P-2xB1-B5/P-Os.Act1-3 | 23 | pMON38305 | 3.6 |
| P-2xA1-B3/P-Os.Act1-1 | 18 | pMON38310 | 4.5 |
| P-2xA1-B3/P-Os.Act1-2 | 19 | pMON38312 | 4.6 |
| P-2xA1-B3/P-Os.Act1-3 | 20 | pMON38314 | 11.0 |
| P-2xB1-B2/P-Os.Act1-1 | 15 | pMON38309 | 1.1 |
| P-2xB1-B2/P-Os.Act1-2 | 16 | pMON38311 | 1.5 |
| P-2xB1-B2/P-Os.Act1-3 | 17 | pMON38313 | 2.2 |
| P-4xAS-1/P-Os.Act1-1 | 12 | pMON38300 | 1.8 |
| P-4xAS-1/P-Os.Act1-2 | 13 | pMON38301 | 1.3 |
| P-4xAS-1/P-Os.Act1-3 | 14 | pMON38302 | 8.9 |
| P-4xB3/P-Os.Act1-1 | 9 | pMON38306 | 1.8 |
| P-4xB3/P-Os.Act1-2 | 10 | pMON38307 | 3.3 |
| P-4xB3/P-Os.Act1-3 | 11 | pMON38308 | 5.4 |
| P-CaMV.e35S | 1 | pMON25456 | 5.1 |

All the chimeric promoters tested were found to have higher activity than the native P-Os.Act1 promoter when tested in corn protoplasts. The three chimeric promoters P-2xA1-B3/P-Os.Act1-3 (SEQ ID NO: 20), P-4xAS-1/P-Os.Act1-3 (SEQ ID NO: 14), and P-4xB3/P-Os.Act1-3 (SEQ ID NO: 11) also showed increased activity when compared to the CaMV e35S promoter. Two factors contributed the enhanced activity in the chimeric promoter, namely the enhancer domain selected and the fusion location of the enhancer domain. Every enhancer domain tested appeared to be more powerful when the fusion location was closer to the 3' end of the promoter, and attenuated when the fusion location was at the 5' end of the promoter. Among the enhancer domains tested, the 2xA1-B3 enhancer was found to be the strongest enhancer domain in corn protoplasts. The 4xAS-1 enhancer was found to convey desirable strength to the chimeric promoter. The 4xB3 enhancer was found to be most effective when fused closer to the transcription start site.

One limitation of expression analysis in the corn protoplast system is that it only represents vegetative tissue. An increased expression level in the corn protoplast system is not necessarily indicative of performance in reproductive tissue. A few selected chimeric promoters were therefore further tested for GUS activity (pmol/min in 10 ul) in wheat anther, wheat ovary, barley microspore, and corn pollen transient assay systems for comparison with corn leaf protoplast data. Data are provided in Table 3 below. In comparison to P-Os.Act1 promoter which is known to express well in reproductive tissue, these chimeric promoters did not show any decrease of activity in reproductive tissue.

TABLE 3

| Transient Analysis of Selected Chimeric Promoters in Reproductive Tissues | | | | | | |
|---|---|---|---|---|---|---|
| Promoter | SEQ ID NO | Construct | Wheat Anther | Wheat Ovary | Barley Microspore | Corn Pollen |
| P-Os.Act1 | 7 | pMON25455 | 1.0 | 1.0 | 1.0 | 1.0 |
| P-CaMV.E35S | 1 | pMON25456 | 3.3 | 0.5 | 0.8 | 0.03 |
| P-4xAS-1/P-Os.Act1-3 | 14 | pMON38302 | 16.4 | 1.2 | 2.0 | 2.2 |
| P-4xB3/P-Os.Act1-2 | 10 | pMON38307 | 1.5 | 2.1 | — | 6.0 |
| P-4xB3/P-Os.Act1-3 | 11 | pMON38308 | 6.4 | 2.5 | — | 0.6 |
| P-2xA1-B3/P-Os.Act1-1 | 18 | pMON38310 | 3.3 | 1.3 | 2.0 | 1.4 |
| P-2xA1-B3/P-Os.Act1-2 | 19 | pMON38312 | 7.6 | 3.3 | 2.4 | 0.5 |
| P-2xA1-B3/P-Os.Act1-3 | 20 | pMON38314 | 13.2 | 3.9 | 7.8 | 0.05 |

Dicot Analysis

Constructs containing chimeric P-At.Act1 promoters were used to transform tobacco protoplasts and assay for GUS activity (nM MUG/μg total protein). Data are provided in Table 4 below.

TABLE 4

| Transient Analysis in Tobacco Protoplasts | | | |
|---|---|---|---|
| Chimeric Promoter | SEQ ID NO | Construct | GUS Activity |
| P-At.Act1 | 8 | pMON54945 | 10 |
| P-2xA1-B3/At.Act1/ArvII | 24 | pMON59394 | 18 |
| P-2xA1-B3/At.Act1/BstZI | 25 | pMON59392 | 20 |
| P-2xA1-B3/At.Act1/BstZI-R | 26 | pMON59392-R | 16 |
| P-2xA1-B3/At.Act1/NsiI | 27 | pMON59386 | 23 |
| P-2xA1-B3/At.Act1/NsiI-R | 28 | pMON59386-R | 12 |
| P-2xA1-B3/At.Act1/BsmFI | 29 | pMON59384 | 65 |
| P-4xAS-1/At.Act1/ArvII | 30 | pMON59393 | 19 |
| P-4xAS-1/At.Act1/ArvII-R | 31 | pMON59393-R | 15 |
| P-4xAS-1/At.Act1/BstZI | 32 | pMON59391 | 16 |
| P-4xAS-1/At.Act1/BstZI-R | 33 | pMON59391-R | 21 |
| P-4xAS-1/At.Act1/NsiI | 34 | pMON59385 | 150 |
| P-4xAS-1/At.Act1/BsmFI | 35 | pMON59383 | 179 |
| P-e35S | 1 | pMON26180 | 365 |

Both the fusion location and choice of enhancer domain was found to produce a significant effect on promoter activity in tobacco protoplasts. The two promoters with the highest GUS activity were the P-4xAS-1/At.Act1/NsiI (SEQ ID NO: 34) and P-4xAS-1/At.Act1/BsmFI (SEQ ID NO: 35). For constructs comprising the 2xA1B3 enhancer, the highest activity of GUS was shown with the enhancer fused at the BsmFI position. The 2xA1-B3 chimeric promoters were generally less active in all positions when compared to the 4xAS-1 chimeric promoters. Reverse orientation of the enhancer domain did not change significantly the activity of the chimeric promoter.

Example 3

Characterization of Chimeric Promoters in Transgenic Corn Plants

Selected chimeric promoters were used for stable corn plant transformation for reporter expression analysis. Plants were transformed using *agrobacterium*-mediated methods.

In order to have a direct side-by-side comparison of GUS activity in the cytoplasm and CP4 expression in plastids, and to minimize variations in sampling and environmental factors, a few selected chimeric promoter constructs were built. Each test construct comprised the test promoter driving the GUS reporter gene (beta-glucuronidase coding sequence from *E. coli*) and the test promoter driving the CP4 gene (bacterial strain CP4 aroA gene encoding class II EPSPS enzyme) in a linear array. Four test constructs, pMON46172 (P-2xA1-B3/P-Os.Act1-3, SEQ ID NO: 20); pMON46173 (P-4xAS-1/P-Os.Act1-3, SEQ ID NO: 14); pMON46174 (P-4-xB3/P-Os.Act1-2, SEQ ID NO: 10); and pMON46175 (P-2xA1-B3/P-Os.Act1-1, SEQ ID NO: 18), and the reference construct, pMON46170 (P-CaMV.E35S driving GUS and P-Os.Act1 driving CP4), were used to transform corn. Transformed corn plants were selected in glyphosate containing medium. Three R0 plants were generated for each transformation event. The first plant was sprayed with the equivalent of 64 ounce/acre of Roundup® Ultra, the second plant was sprayed with the equivalent of 96 ounce/acre of Roundup® Ultra. The third plant from each event was left as unsprayed control. Ten to fourteen days after Roundup® application each plant was rated for % chlorosis and % malformation. At mid-pollen shed, each R0 plant was rated for male fertility. Positive R0 plants were pollinated with LH198 pollen grains to produce F1 seed.

Transgenic events with single or lowest copy numbers of cassette based on CP4 copy number estimation by Taqman were selected for F1 corn analysis. A total of 5 events from each construct with triplicate plants in each data point were used. The plants were grown in greenhouse from F1 seeds, and selected for positive segregates via glyphosate spray at 16 oz/acre when plants reach V-2 stage. Leaf tissue was taken at V-4 stage, and V-4 again at V-8/V-9 stage. Also at V-8/V-9 stage, tissue was collected from V-8 leaf, root tip, and immature tassel ranging from 0.5 cm-3 cm. Pollen was collected when shedding. Embryo and endosperm were harvested at 12 days after pollination. Several positive embryos were pooled from GUS positive individual kernels. Samples were extracted and used for both GUS quantitative analysis and CP4 ELISA. The P-2xA1-B3/P-Os.Act1-3 and P-4xAS-1/P-Os.Act1-3 chimeric promoters provided GUS gene expression which was as good as or better than that provided by P-CaMV.E35S in most of the tissues analyzed. The P-4-xB3/P-Os.Act1-2 and P-2xA1-B3/P-Os.Act1-1 chimeric promoters provided high levels of expression in pollen with moderate or low levels of expression in other tissues as compared to that provided by P-CaMV.E35S. The Data are provided for GUS activity (pmole/min/mg protein) as mean and standard error measurements in Table 5 below.

TABLE 5

F1 Transgenic Corn GUS Activity (pmole/min/mg protein)

| | pmon46170 P-CaMV.E35S | | pmon46172 P-2xA1-B3/P-Os.Act1-3 | | pmon46173 P-4xAS-1/P-Os.Act1-3 | | pmon46174 P-4xB3/P-Os.Act1-2 | | pmon46175 P-2xA1-B3/P-Os.Act1-1 | |
|---|---|---|---|---|---|---|---|---|---|---|
| Tissue/Stage | Mean | SE | Mean | SE | Mean | SE | Mean | SE | Mean | SE |
| Young V4 | 6.54 | 0.29 | 12.28 | 3.00 | 5.11 | 0.75 | 1.02 | 0.35 | 5.70 | 0.60 |
| Aged V4 | 2.82 | 0.85 | 6.47 | 1.43 | 6.78 | 1.59 | 0.10 | 0.02 | 4.14 | 1.09 |
| V8 | 0.67 | 0.20 | 1.27 | 0.51 | 0.64 | 0.12 | 0.17 | 0.05 | 0.13 | 0.01 |
| Tassel | 0.57 | 0.19 | 0.49 | 0.25 | 0.50 | 0.23 | 0.19 | 0.07 | 0.13 | 0.07 |
| Root Tip | 0.38 | 0.04 | 0.84 | 0.10 | 1.11 | 0.43 | 0.19 | 0.04 | 0.97 | 0.38 |
| Pollen | 1.44 | 0.11 | 2.27 | 0.26 | 2.87 | 0.52 | 15.26 | 2.84 | 13.76 | 2.05 |
| Embryo | 2.19 | 0.22 | 2.35 | 0.68 | 5.68 | 1.64 | 1.42 | 0.18 | 2.53 | 0.65 |
| Endosperm | 1.73 | 0.15 | 9.21 | 4.35 | 6.18 | 1.59 | 1.40 | 0.51 | 2.09 | 0.37 |

All four chimeric promoters provided CP4 gene expression which was as good as or better than that provided by P-Os.Act1 in all of the tissues analyzed with the exception of pollen. Expression levels in pollen for chimeric promoter constructs were approximately 20% to 73% that of expression levels in pollen for P-Os.Act1 constructs. Data are provided for CP4 expression levels (μg CP4 protein/g total protein) as mean and standard error measurements in Table 6 below.

TABLE 6

F1 Transgenic Corn CP4 Expression levels (μg CP4 protein/g total protein)

| | pmon46170 and P-Os.Act1 | | pmon46172 P-2xA1-B3/P-Os.Act1-3 | | pmon46173 P-4xAS-1/P-Os.Act1-3 | | pmon46174 P-4xB3/P-Os.Act1-2 | | pmon46175 P-2xA1-B3/P-Os.Act1-1 | |
|---|---|---|---|---|---|---|---|---|---|---|
| Tissue/Stage | Mean | SE | Mean | SE | Mean | SE | Mean | SE | Mean | SE |
| Young V4 | 31 | 3 | 35 | 2 | 408 | 122 | 280 | 66 | 952 | 540 |
| Aged V4 | 20 | 2 | 2187 | 656 | 1802 | 411 | 524 | 257 | 688 | 298 |
| V8 | 17 | 2 | 1055 | 298 | 870 | 272 | 311 | 35 | 284 | 110 |
| Tassel | 225 | 27 | 1334 | 515 | 1002 | 178 | 408 | 31 | 1072 | 303 |
| Root Tip | 89 | 8 | 745 | 185 | 765 | 173 | 184 | 22 | 279 | 68 |
| Pollen | 797 | 97 | 165 | 13 | 217 | 33 | 370 | 16 | 582 | 74 |
| Embryo | 241 | 54 | 623 | 69 | 1101 | 187 | 305 | 69 | 566 | 84 |
| Endosperm | 229 | 21 | 792 | 212 | 889 | 229 | 237 | 36 | 375 | 46 |

The F1 progenies were also used for field tests. Three F1 populations derived from three R0 plants of each event were tested. Commercial Roundup Ready® corn lines GA21 and NK603 were used as positive controls. Three Roundup® rates were used in this test: 0, 96, and 128 oz/A. Roundup® was applied at V4 leaf stage. Data obtained were % transformation efficiency (TE), number of single copy events per total events generated, Leaf CP4 levels (μgCP4/g fresh weight tissue), Pollen CP4 levels (μgCP4/g fresh weight tissue), percent chlorosis (CHL), percent malformation (MAL) at 10-14 DAT (days after treatment), and male fertility score (MFR) measured 1-5 with 5 the highest. Data represent the average score collected across the events generated for each construct and only tasseled plants were included for some measurements. Plants transformed with the P-4-xB3/P-Os.Act1-2 or the P-4xAS-1/P-Os.Act1-3 chimeric promoter constructs had chlorosis scores equivalent to the reference construct (pMON46170). P-4xAS-1/P-Os.Act1-3 had a malformation score lower than that of the reference construct. All chimeric promoters tested had male fertility rates comparable to that of plants transformed with the reference construct. Data are provided in Table 7 below.

TABLE 7

Roundup ® Tolerance in Transgenic Corn Field Tests

| Promoter | Construct | % TE | Single Copy | Leaf CP4 | Pollen CP4 | Pollen GUS | % CHL | % MAL | MFR |
|---|---|---|---|---|---|---|---|---|---|
| P-CaMV.E35S and P-Os.Act1 | pMON46170 | 12 | 7/15 | 22 | 1471 | 4.4 | 1 | 1 | 5 |
| P-2xA1-B3/P-Os.Act1-3 | pMON46172 | 10 | 5/15 | 116 | 313 | 5.8 | 7 | 4 | 5 |
| P-4xAS-1/P-Os.Act1-3 | pMON46173 | 16 | 9/15 | 319 | 475 | 9.7 | 1 | 0 | 5 |
| P-4xB3/P-Os.Act1-2 | pMON46174 | 24 | 8/15 | 78 | 674 | 24.3 | 1 | 3 | 5 |
| P-2xA1-B3/P-Os.Act1-1 | pMON46175 | — | 1/15 | 77 | 767 | 34.1 | 2 | 3 | 5 |

Example 4

Characterization of Chimeric Promoters in Transgenic Dicots

Several constructs were evaluated in transgenic *Arabidopsis* plants for GUS expression. GUS expression in leaf and flower tissue was measured as pM MUG/μg total protein and results were averaged for all the events produced for construct. The CaMV e35S promoter (P-CaMV.e35S) and *Arabidopsis* actin 1 promoter (P-At.Act1) were used as controls. Data are provided in Table 8 below

TABLE 8

Transgenic *Arabidopsis* analysis with chimeric At-Act1 promoters

| Promoter | SEQ ID NO | Construct | Flower | Leaf |
|---|---|---|---|---|
| P-At.Act1 | 8 | pMON59382 | 139 | 62 |
| P-CaMV.e35S | 1 | pMON59381 | 374 | 176 |
| P-2xA1-B3/At.Act1/BstZI | 25 | pMON59378 | 0 | 24 |
| P-4xAS-1/At.Act1/BstZI | 32 | pMON59377 | 12 | 47 |
| P-4xAS-1/At.Act1/ArvII | 30 | pMON59379 | 58 | 18 |
| P-4xAS-1/At.Act1/NsiI | 34 | pMON59375 | 46 | 36 |
| P-4xAS-1/At.Act1/BstZI-R | 33 | pMON59371 | 66 | 21 |
| P-2xA1-B3/At.Act1/NsiI | 27 | pMON59376 | 113 | 56 |
| P-2xA1-B3/At.Act1/BstZI-R | 26 | pMON59372 | 149 | 114 |
| P-4xAS-1/At.Act1/BsmFI | 35 | pMON59373 | 29 | 256 |
| P-2xA1-B3/At.Act1/ArvII | 24 | pMON59380 | 88 | 199 |
| P-2xA1-B3/At.Act1/BsmFI | 29 | pMON59374 | 153 | 193 |

GUS expression analysis in *Arabidopsis* showed that P-2xA1-B3/At.Act1/BstZI-R (SEQ ID NO: 26) and P-2xA1-B3/At.Act1/BsmFI (SEQ ID NO: 29) provided transgene expression in flowers comparable to that of the P-At.Act1 promoter. The P-2xA1-B3/At.Act1/BstZI-R (SEQ ID NO: 26), P-4xAS-1/At.Act1/BsmFI (SEQ ID NO: 35), P-2xA1-B3/At.Act1/ArvII (SEQ ID NO: 24), and P-2xA1-B3/At.Act1/BsmFI (SEQ ID NO: 29) promoters provided transgene expression in leaves higher than or comparable to the P-At.Act1 and P-CaMV.e35S.

Example 4

Insect Control Analysis in Corn

Two constructs (pMON38858 and pMON38859) were used to generate transgenic corn plants. Transformations were performed using *Agrobacterium* mediated methods. Both constructs contained the 2xA1-B3/P-Os.Act1-3 promoter (SEQ ID NO: 20) operably linked to a nucleotide sequence encoding a Cry2Ab insecticidal protein (U.S. Pat. No. 6,489,542). Several transgenic corn plant lines produced from each construct were analyzed for Cry2Ab protein levels. The 2xA1-B3/P-Os.Act1-3 promoter was found to express the Cry2Ab protein at high levels in corn leaf tissue when compared with standard controls.

Example 5

Glyphosate Tolerance Analysis in Wheat

Three chimeric promoters were tested in transgenic wheat plants. Transgenic wheat plants were generated from each of the single cassette constructs pMON43646 (P-4xAS-1/P-Os.Act1-3, SEQ ID NO: 14), pMON43647 (P-2xA1-B3/P-Os.Act1-2, SEQ ID NO: 19), and pMON43648 (P-2xA1-B3/P-Os.Act1-3, SEQ ID NO: 20). Transformations were performed with *Agrobacterium* in immature Bobwhite embryos. All three constructs contain a single copy of the CP4 EPSPS gene for glyphosate tolerance. The distinguishing element in each construct is the promoter. Events from each single cassette construct were analyzed for vegetative and reproductive tolerance to glyphosate equivalent to the double cassette lead event 33391 (U.S. Patent Publication US20020062503) generated from pMON30139 which contains two copies of the CP4 EPSPS gene driven by the P-e35S and P-Os.Act1 promoters, respectively. Plants were analyzed for glyphosate tolerance, phenotype, copy number, molecular profile, and genome location. Results are provided below.

R0 plants were spray tested for vegetative and reproductive tolerance with 64 oz/A Roundup® Ultra (1.68 kg/ha acid equivalents of glyphosate) prior to jointing. Plants with vegetative damage were discarded. Fertility was estimated by counting the number of seeds in 20 florets from the central portion of the head and reported as % fertility. Data are provided in Table 9 below.

TABLE 9

Glyphosate Tolerance in Transgenic R0 Wheat Plants

| Promoter | Construct | R0 Events | # Events with Vegetative Tolerance (% of total) | # Events with >=80% Fertility (% with Veg Tol) |
|---|---|---|---|---|
| P-Os.Act1 | pMON30167 | 63 | 4 (6%) | 2 (50%) |
| P-CaMV.e35S and P-Os.Act1 | pMON30139 | 150 | 104 (69%) | 24 (23%) |
| P-4xAS-1/P-Os.Act1-3 | pMON43646 | 87 | 65 (75%) | 13 (20%) |
| P-2xA1-B3/P-Os.Act1-2 | pMON43647 | 83 | 61 (73%) | 16 (26%) |
| P-2xA1-B3/P-Os.Act1-3 | pMON43648 | 69 | 51 (74%) | 12 (24%) |

Data on the vegetative and reproductive glyphosate tolerance of R0 wheat plants transformed with a single cassette vector containing CP4 driven by the rice actin promoter (pMON30167) and a double cassette vector containing two CP4 genes driven by P-CaMV.e35s and P-Os.Act1 are also provided in Table 15. Wheat transformation experiments that used the P-CaMV.e35S cassette alone resulted in plants that were vegetatively tolerant but had low fertility. For example plants generated with pMON42411, comprising only the P-CaMV.e35S promoter driving the CP4 gene, produced only 1 of 37 vegetatively tolerant plants with a fertility of >=80%. This data indicates that the e35S promoter is responsible for vegetative expression of CP4 while the rice actin promoter is responsible for reproductive expression of CP4. Results for the single cassette vector containing the three chimeric promoters (pMON43646, pMON43647, and pMON43648) were similar to those for the double cassette vector pMON30139. 73-75% of the total events generated using these three chimeric promoter constructs had vegetative tolerance, and 20-26% of those events had >=80% fertility. Thus, using one of the three chimeric promoters to drive a single copy of the CP4 EPSPS gene produced similar results in R0 tests as double cassette lead event.

In addition to glyphosate tolerance, transformation efficiencies (TE), leaf CP4 levels (μgCP4/mg total protein from R0 wheat plants), and meristem CP4 levels (μgCP4/mg total protein from R0 wheat plants) were measured in R0 plants. Plants transformed with pMON30139 (the double cassette construct) and pMON30159 (P-ScBV see U.S. Pat. No. 6,489,462) were used as controls. Data are provided in Table 10 below.

TABLE 10

CP4 Expression in Transgenic R0 Wheat Plants

| Promoter | Construct | TE | Leaf CP4 | Meristem CP4 |
|---|---|---|---|---|
| P-CaMV.e35S and P-Os.Act1 | pMON30139 | 4% | 2.23 (0.93%) | 4.54 (1.48%) |
| P-ScBV | pMON30159 | 4.50% | 6.99 (1.43%) | 9.7 (1.71%) |

TABLE 10-continued

CP4 Expression in Transgenic R0 Wheat Plants

| Promoter | Construct | TE | Leaf CP4 | Meristem CP4 |
|---|---|---|---|---|
| P-4xAS-1/P-Os.Act1-3 | pMON43646 | 3.30% | 2.13 (.99%) | 3.72 (1.55%) |

TABLE 10-continued

CP4 Expression in Transgenic R0 Wheat Plants

| Promoter | Construct | TE | Leaf CP4 | Meristem CP4 |
|---|---|---|---|---|
| P-2xA1-B3/P-Os.Act1-2 | pMON43647 | 2.90% | 1.41 (1%) | 1.66 (1.23%) |
| P-2xA1-B3/P-Os.Act1-3 | pMON43648 | 2.20% | 4.62 (0.77%) | 5.79 (1.31%) |

R1 seeds were then collected from the R0 plants and advanced to R1 testing. R1 plants were simultaneously tested for glyphosate tolerance and copy number. The transgene copy number for each event was determined by Southern blot and/or TaqMan quantitative PCR analysis. CP4 gene sequences were used as probes for both assays. A good correlation was observed between single copy calls on Southerns and by TaqMan analysis. Single copy events, with good tolerance to high doses of glyphosate, were advanced to the R2 generation.

Seeds from selected wheat lines advanced to the R2 generation were planted in 2" pots and sprayed with 128 oz/A Roundup at the 3 leaf stage. Retained lines were transferred to larger pots and sprayed again with 128 oz/A at the 6 leaf stage. In an attempt to force differentiation among events an extreme pressure test was devised where plants were sprayed with 512 oz/A of Roundup®. This was repeated four times between the 3 leaf stage and emergence of the flag leaf. Results for the chimeric promoter lines were compared with results for non-transgenic Bobwhite plants, R4 generation lead event plants (line 33391 generated from pMON30139), and R3 generation plants containing the P-ScBV promoter (line TA_S2520 generated from pMON30159). Yield data (grams) and fertility data (as % of total plants) were collected for each line. Data are provided in Table 11 below.

TABLE 11

Pressure Test of R2 Wheat Plants

| Promoter | Construct | Line | Yield (g) | Fertility (%) |
|---|---|---|---|---|
| N/A | N/A | Non-transgenic Bobwhite | 23.1 | 93.5 |
| P-CaMV.e35S and P-Os.Act1 | pMON30139 | 33391 | 24.1 | 91.2 |
| P-ScBV | pMON30159 | TA_S2520 | 21.0 | 87.5 |
| P-2xA1-B3/P-Os.Act1-2 | pMON43647 | TA_S7535 | 22.2 | 91.5 |
| P-2xA1-B3/P-Os.Act1-2 | pMON43647 | TA_S7890 | 23.0 | 95.8 |
| P-2xA1-B3/P-Os.Act1-2 | pMON43647 | TA_S9215 | 21.5 | 95.2 |
| P-4xAS-1/P-Os.Act1-3 | pMON43646 | TA_S9240 | 20.6 | 95.0 |

From this analysis it is apparent that the use of the P-4xAS-1/P-Os.Act1-3 (SEQ ID NO: 14), P-2xA1-B3/P-Os.Act1-2 (SEQ ID NO: 19), and P-2xA1-B3/P-Os.Act1-3 (SEQ ID NO: 20) promoters in plant CP4 expression cassettes confers glyphosate tolerance to vegetative tissues in wheat plants without negatively impacting fertility. In wheat, cassettes containing the rice actin promoter without these elements produce plants with low vegetative tolerance and are not useful for the production of glyphosate tolerant plants. Therefore one advantage of the chimeric promoters in wheat is that vegetative and reproductive tolerance can be achieved without the use of a double CP4 cassette.

Field trails were performed with R4 generation plants to assess the performance of selected lines. Field trails were done at eight US sites with 4 replications each and treatments of 0, 64, and 128 oz/A Roundup® Ultra equivalent. Each treatment was arranged as a separate, randomized complete block in order to collect equivalence data on unsprayed non-transformed Bobwhite plants. All events had vegetative and reproductive tolerance comparable to the lead event 33391 at doses up to 128 oz/A of Roundup® Ultra. Yield was measured in tons/hectar (T/ha). Data are provided in Table 12 below.

TABLE 12

Yield Data from Field Trials of R4 Plants (T/ha)

| Promoter | Construct | Line | 128 oz/A | 64 oz/A | No spray |
|---|---|---|---|---|---|
| P-CaMV.e35S and P-Os.Act1 | pMON30139 | 33391 | 3.52 | 3.58 | 3.63 |
| P-ScBV | pMON30159 | TA_S2520 | 3.78 | 3.79 | 3.69 |
| P-2xA1-B3/P-Os.Act1-2 | pMON43647 | TA_S7535 | 3.72 | 3.68 | 3.51 |
| P-2xA1-B3/P-Os.Act1-2 | pMON43647 | TA_S7890 | 3.79 | 3.72 | 3.70 |
| P-2xA1-B3/P-Os.Act1-2 | pMON43647 | TA_S9215 | 3.59 | 3.57 | 3.42 |
| P-4xAS-1/P-Os.Act1-3 | pMON43646 | TA_S9240 | 3.58 | 3.81 | 3.66 |

Having illustrated and described the principles of the present invention, it should be apparent to persons skilled in the art that the invention can be modified in arrangement and detail without departing from such principles. We claim all modifications that are within the spirit and scope of the appended claims. All publications and published patent documents cited in this specification are incorporated herein by reference to the same extent as if each individual publication or patent application is specifically and individually indicated to be incorporated herein by reference.

We claim:

1. A chimeric promoter comprising SEQ ID NO:18.

2. A construct comprising the chimeric promoter of claim 1, wherein said chimeric promoter is operably linked to a transcribable polynucleotide molecule operably linked to a 3' transcription termination polynucleotide molecule.

3. The construct of claim 2, wherein said transcribable polynucleotide molecule is a marker gene.

4. The construct of claim 2, wherein said transcribable polynucleotide molecule is a gene of agronomic interest.

5. The construct of claim 4, wherein said gene of agronomic interest is a herbicide tolerance gene selected from the group consisting of genes that encode for phosphinothricin acetyltransferase, glyphosate resistant 5-enolpyruvylshikimate-3-phosphate synthase, hydroxyphenyl pyruvate dehydrogenase, dalapon dehalogenase, bromoxynil resistant nitrilase, anthranilate synthase, glyphosate oxidoreductase, dicamba monooxygenase, and glyphosate-N-acetyl transferase.

6. A transgenic plant stably transformed with the construct of claim 2.

7. The transgenic plant of claim 6, wherein said transcribable polynucleotide is a gene of agronomic interest.

8. The transgenic plant of claim 6, wherein said transcribable polynucleotide is a marker gene.

9. A seed stably transformed with the construct of claim 2.

10. A method of inhibiting weed growth in a field of transgenic glyphosate crop plants comprising:

i. planting transgenic plants transformed with the construct of claim 2, wherein said transcribable polynucleotide comprises a DNA molecule encoding a glyphosate tolerance gene and ii. applying glyphosate to the field at an application rate that inhibits the growth of weeds, wherein the growth and yield of the transgenic crop plant is not substantially affected by the glyphosate application.

11. In the method of claim 10, wherein said glyphosate tolerance gene is selected from the group consisting of a gene encoding for a glyphosate resistant 5-enolpyruvylshikimate-3-phosphate synthase, a glyphosate oxidoreductase, and a glyphosate-N-acetyltransferase.

12. In the method of claim 10, wherein the transgenic plants are capable of tolerating an application rate up to 256 ounces/acre.

13. In the method of claim 10, wherein the transgenic plants are capable of tolerating an application rate ranging from 8 ounces/acre to 128 ounces/acre.

14. In the method of claim 10, wherein the transgenic plants are capable of tolerating an application rate ranging from 32 ounces/acre to 96 ounces/acre.

15. In the method of claim 10, wherein the application of glyphosate is at least once during the growth of the crop.

* * * * *

UNITED STATES PATENT AND TRADEMARK OFFICE

CERTIFICATE OF CORRECTION

PATENT NO. : 8,436,161 B2
APPLICATION NO. : 12/876071
DATED : May 7, 2013
INVENTOR(S) : Timothy W. Conner et al.

It is certified that error appears in the above-identified patent and that said Letters Patent is hereby corrected as shown below:

In the Claims

Column 72, Line 57, please delete "glyphosate crop" and insert --glyphosate tolerant crop--

Column 72, Line 59, please delete "polynucleotide comprises" and insert --polynucleotide molecule comprises--

Signed and Sealed this
Thirteenth Day of August, 2013

Teresa Stanek Rea
*Acting Director of the United States Patent and Trademark Office*